United States Patent
Denzinger

(10) Patent No.: US 12,383,274 B1
(45) Date of Patent: Aug. 12, 2025

(54) SHAFT DEFLECTION DETECTION SYSTEM FOR A SURGICAL INSTRUMENT

(71) Applicant: Cilag GmbH International, Zug (CH)

(72) Inventor: Christopher Denzinger, Loveland, OH (US)

(73) Assignee: Cilag GmbH International, Zug (CH)

( * ) Notice: Subject to any disclaimer, the term of this patent is extended or adjusted under 35 U.S.C. 154(b) by 0 days.

(21) Appl. No.: 18/634,029

(22) Filed: Apr. 12, 2024

(51) Int. Cl.
| | |
|---|---|
| A61B 17/068 | (2006.01) |
| A61B 17/11 | (2006.01) |
| A61B 17/115 | (2006.01) |
| A61B 34/30 | (2016.01) |
| A61B 90/00 | (2016.01) |
| A61B 17/00 | (2006.01) |

(52) U.S. Cl.
CPC .......... *A61B 17/1155* (2013.01); *A61B 34/30* (2016.02); *A61B 90/06* (2016.02); *A61B 2017/00039* (2013.01); *A61B 2017/00119* (2013.01); *A61B 2017/00477* (2013.01); *A61B 2034/302* (2016.02); *A61B 2090/064* (2016.02)

(58) Field of Classification Search
CPC .............. A61B 17/068; A61B 17/072; A61B 17/1155; A61B 34/70; A61B 34/77
See application file for complete search history.

(56) References Cited

U.S. PATENT DOCUMENTS

| | | | |
|---|---|---|---|
| 5,292,053 A | 3/1994 | Bilotti | |
| 5,333,773 A | 8/1994 | Main | |
| 5,350,104 A | 9/1994 | Main | |
| 5,533,661 A | 7/1996 | Main | |
| 6,970,308 B2 * | 11/2005 | Otsuka | H04N 23/55 |
| | | | 348/E5.028 |
| 8,083,691 B2 * | 12/2011 | Goldenberg | A61B 5/6885 |
| | | | 600/587 |
| 8,210,411 B2 | 7/2012 | Yates et al. | |
| 8,910,847 B2 | 12/2014 | Nalagatla | |
| 9,186,142 B2 | 11/2015 | Fanelli et al. | |
| 9,517,065 B2 | 12/2016 | Simms et al. | |
| 9,519,341 B2 * | 12/2016 | Hasegawa | A61B 34/76 |
| 9,622,746 B2 | 4/2017 | Simms et al. | |
| 9,713,469 B2 | 7/2017 | Leimbach | |
| 9,717,497 B2 | 8/2017 | Zerkle et al. | |
| 9,795,379 B2 | 10/2017 | Leimbach et al. | |
| 9,808,248 B2 | 11/2017 | Hoffman | |
| 9,839,421 B2 | 12/2017 | Zerkle et al. | |
| 9,907,552 B2 | 3/2018 | Measamer | |
| 9,936,949 B2 | 4/2018 | Measamer | |

(Continued)

*Primary Examiner* — Gloria R Weeks
(74) *Attorney, Agent, or Firm* — Lempia Summerfield Katz LLC

(57) ABSTRACT

A surgical instrument includes a shaft deflection detection system including one or more sensors positioned at a first mechanical junction between a shaft and an actuator coupled with the shaft and/or a second mechanical junction between the shaft and an end effector coupled with the shaft. The shaft is movable relative to the actuator at the first mechanical junction and/or relative to the end effector at the second mechanical junction. The one or more sensors are configured to generate signals indicative of movement of the shaft relative to the actuator and/or the end effector. The movement of the shaft is caused by an external force experienced by the shaft as the shaft of the surgical instrument is maneuvered inside a body of a patient.

20 Claims, 19 Drawing Sheets

(56) References Cited

U.S. PATENT DOCUMENTS

| | | | |
|---|---|---|---|
| 10,092,292 | B2 | 10/2018 | Boudreaux et al. |
| 10,182,813 | B2 | 1/2019 | Leimbach et al. |
| 10,653,420 | B2 * | 5/2020 | Scheib ................. A61B 17/068 |
| 10,709,452 | B2 | 7/2020 | Dinardo |
| 11,304,697 | B2 | 4/2022 | Fanelli et al. |
| 11,317,912 | B2 | 5/2022 | Jenkins et al. |
| 11,376,082 | B2 * | 7/2022 | Shelton, IV ... A61B 17/320068 |
| 11,439,391 | B2 | 9/2022 | Bruns et al. |
| 11,547,468 | B2 * | 1/2023 | Shelton, IV ....... A61B 18/1815 |
| 2015/0083772 | A1 | 3/2015 | Miller |
| 2018/0132849 | A1 | 5/2018 | Miller |
| 2022/0378538 | A1 * | 12/2022 | Kanazawa ............. A61B 34/25 |

* cited by examiner

SHAFT DEFLECTION DETECTION SYSTEM FOR A SURGICAL INSTRUMENT

BACKGROUND

Surgical instruments, such as surgical staplers, may be used in various manual and/or robotic surgical procedures. For example, a circular surgical stapler may be used to provide an end-to-end, side-to-side, or end-to-side anastomosis between two sections of an anatomical lumen such as a portion of a patient's digestive tract. In some settings, laparoscopic or endoscopic surgical instruments may be preferred over traditional open surgical instruments to minimize the size of the surgical incision as well as post-operative recovery time and complications. Endoscopic surgical instruments may be suitable for placement of the end effector at a desired surgical site through the cannula of a trocar. With various surgical instruments, distal end effectors may engage tissue in a number of ways to achieve a diagnostic or therapeutic effect (e.g., endocutter, grasper, cutter, stapler, clip applier, access device, drug/gene therapy delivery device, and energy delivery device using ultrasound, RF, laser, etc.). Some such surgical instruments are operable to clamp down on layers of tissue, cut through the clamped layers of tissue, and drive staples through the layers of tissue to substantially seal the severed layers of tissue together near the severed ends of the tissue layers. Such endoscopic surgical staplers may also be used in open procedures and/or other non-endoscopic procedures. By way of example only, a surgical stapler may be inserted through a thoracotomy and thereby between a patient's ribs to reach one or more organs in a thoracic surgical procedure that does not use a trocar as a conduit for the stapler. Such procedures may include the use of the stapler to sever and close a vessel leading to an organ, such as a lung. For instance, the vessels leading to an organ may be severed and closed by a stapler before removal of the organ from the thoracic cavity. Of course, surgical staplers may be used in various other settings and procedures.

Surgical instruments suitable for use in open or endoscopic procedures may include a shaft that extends proximally from the end effector to an actuator, such as a manually operated handle portion which is manipulated by the clinician, or a robotic arm operated by a robot. Such a shaft may enable insertion to a desired depth and rotation about the longitudinal axis of the shaft, thereby facilitating positioning of the end effector within the patient. Positioning of an end effector may be further facilitated through inclusion of one or more articulation joints or features, enabling the end effector to be selectively articulated or otherwise deflected relative to the longitudinal axis of the shaft.

During such open or endoscopic surgical procedures, it is important to ensure that the shaft of the surgical instrument is not being too forcefully maneuvered inside a body of a patient during the procedure, for example during insertion of the surgical instrument into a body of a patient and/or removal of the surgical instrument from the body of the patient, in order to ensure that surrounding anatomy (e.g., lumens, veins, arteries, nerves, etc.) is not harmed during the surgical procedure.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the present invention.

Figure 1:
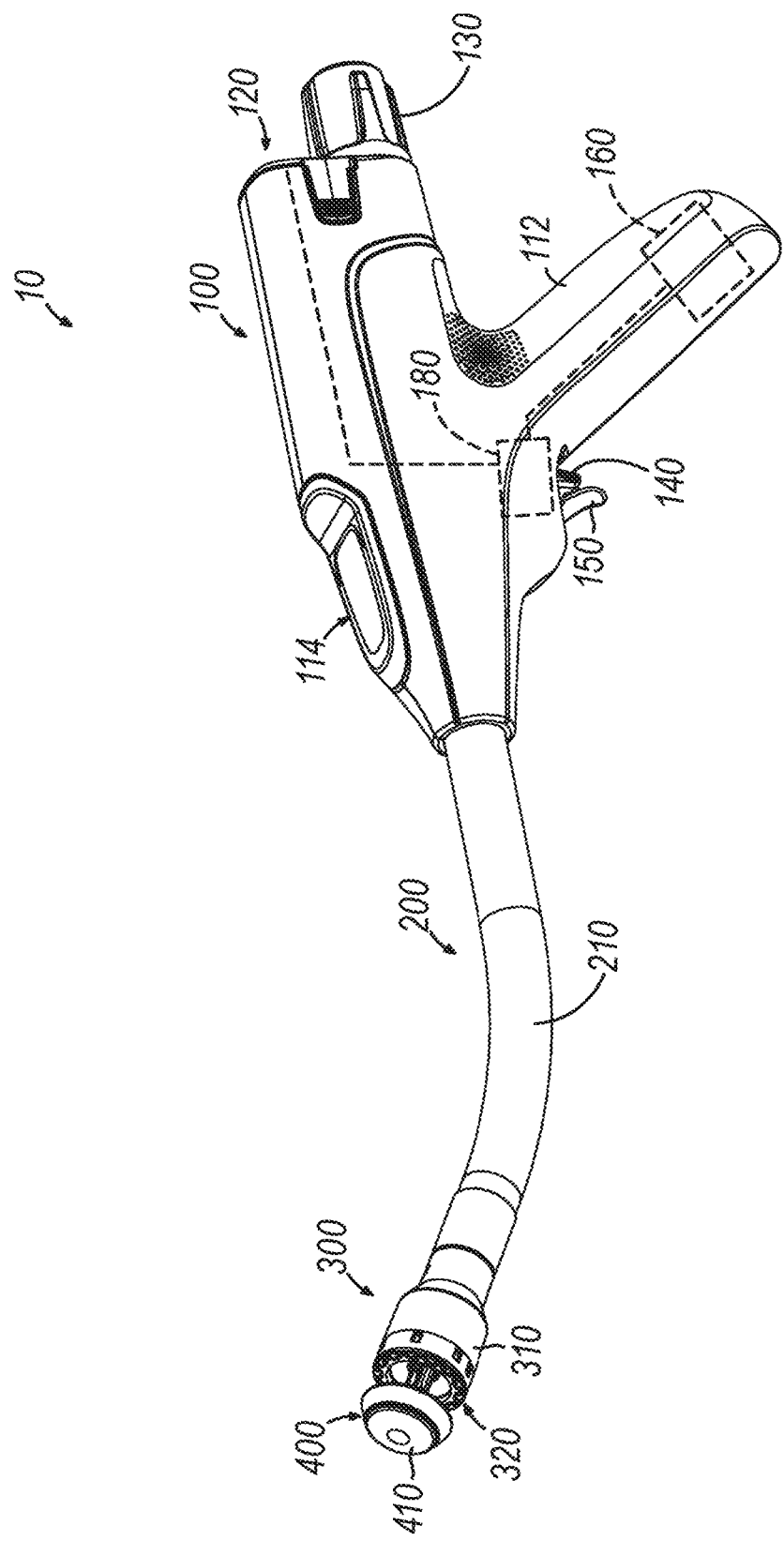
FIG. 1 depicts a perspective view of an example surgical instrument in the form of a circular surgical stapler that includes a handle assembly, a shaft assembly, and an end effector having a stapling head and an anvil.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the technology should not be used to limit its scope. Other examples, features, aspects, embodiments, and advantages of the technology will become apparent to those having ordinary skill in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

For clarity of disclosure, the terms "proximal" and "distal" are defined herein relative to a human or robotic operator of the surgical instrument. The term "proximal" refers to the position of an element closer to the human or robotic operator of the surgical instrument and further away from the surgical end effector of the surgical instrument. The term "distal" refers to the position of an element closer to the surgical end effector of the surgical instrument and further away from the human or robotic operator of the surgical instrument. In addition, the terms "upper," "lower," "lateral," "transverse," "bottom," "top," are relative terms to provide additional clarity to the figure descriptions provided below. The terms "upper," "lower," "lateral," "transverse," "bottom," "top," are thus not intended to unnecessarily limit the invention described herein.

Furthermore, the terms "about," "approximately," "substantially," and the like as used herein in connection with any numerical values, ranges of values, and/or geometric/positional quantifications are intended to encompass the exact value(s) or quantification(s) referenced as well as a suitable tolerance that enables the referenced feature or combination of features to function for the intended purpose described herein. For example, "substantially parallel" encompasses nominally parallel structures.

As used herein in connection with various examples of end effector jaw tips, a tip described as "angled," "bent," or "curved" encompasses tip configurations in which a longitudinal path (e.g., linear or arcuate) along which the tip extends is non-coaxial and non-parallel with a longitudinal axis of the jaw body; particularly, configurations in which the longitudinal tip path extends distally toward the opposing jaw. Conversely, a tip described as "straight" encompasses tip configurations in which a longitudinal axis of the tip is substantially parallel or coaxial with the longitudinal axis of the jaw body.

I. Illustrative Surgical Instrument

Figure 2:
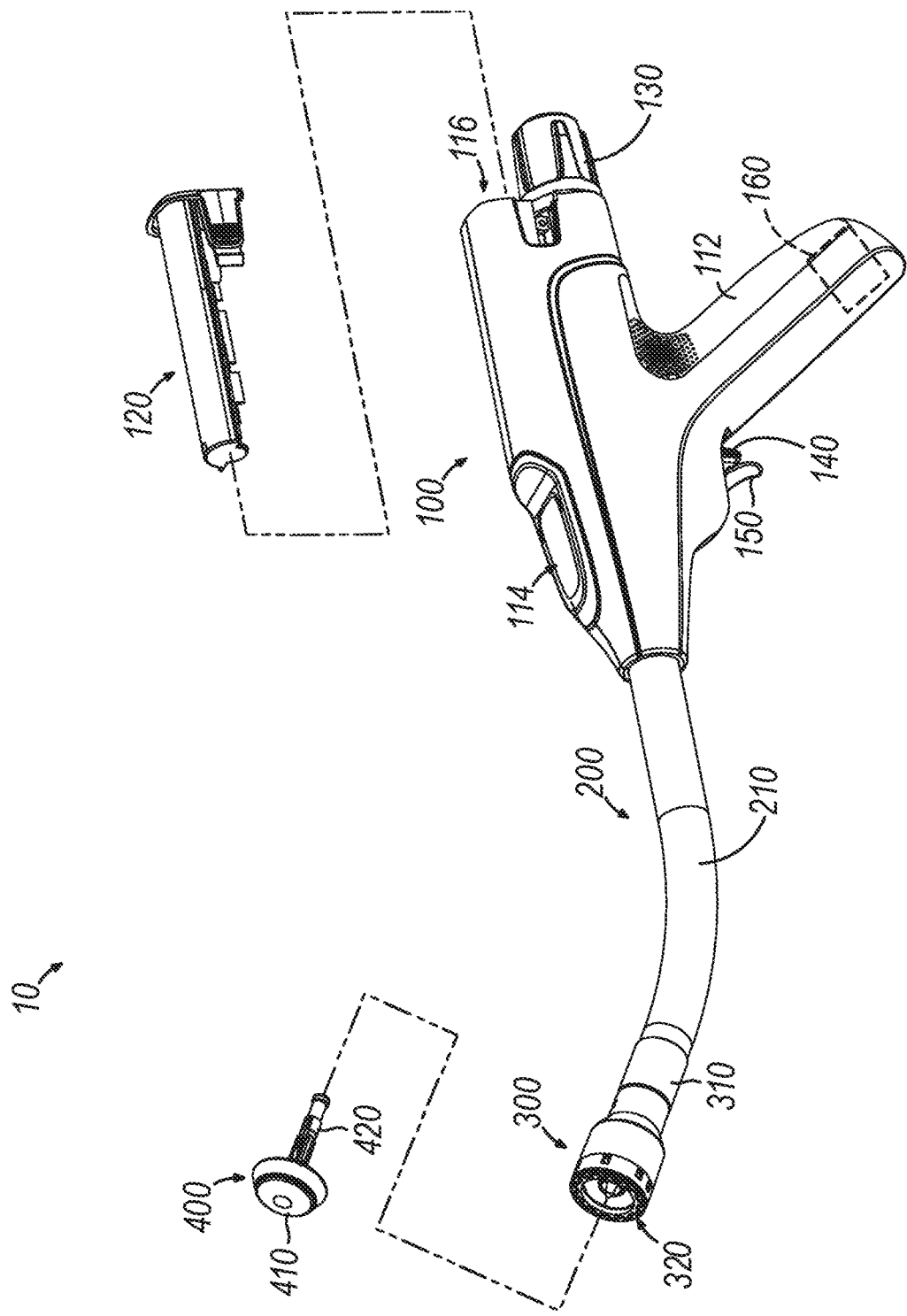
FIG. 2 depicts a perspective view of the surgical instrument of FIG. 1, with a battery pack removed from the handle portion and the anvil separated from the stapling head assembly.

FIGS. 1-2 depict an example surgical instrument 10 that may be used to provide an end-to-end, side-to-side, or end-to-side anastomosis between two sections of an anatomical lumen such as a portion of a patient's digestive tract. Surgical instrument 10 of this example is a circular surgical stapler and includes a body assembly in the form of an actuator such as a manually operated handle portion 100, a shaft 200 extending distally from handle portion 100, an end effector in the form of a stapling head 300 at a distal end of shaft 200 and an anvil 400 configured to releasably couple and cooperate with stapling head 300 to clamp, staple, and cut tissue. Instrument 10 further includes a removable battery pack 120 operable to provide electrical power to a motor 160 housed within handle 100, as described in greater detail below.

As shown in FIGS. 1-2, and as described in greater detail below, anvil 400 is configured to removably couple with shaft 200, adjacent to stapling head 300. As also described in greater detail below, anvil 400 and stapling head 300 are configured to cooperate to manipulate tissue in three ways, including clamping the tissue, cutting the tissue, and stapling the tissue. A rotatable knob 130 at the proximal end of handle 100 is rotatable to provide precise clamping of the tissue between anvil 400 and stapling head 300. When a safety trigger 140 of handle 100 is pivoted away from a firing trigger 150 of handle 100, firing trigger 150 may be actuated to thereby provide cutting and stapling of the clamped tissue.

Figure 3:
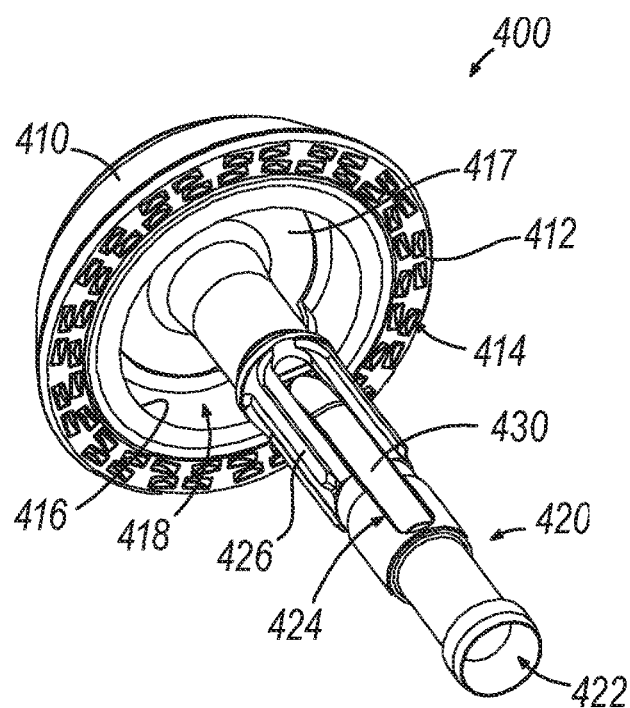
FIG. 3 depicts a perspective view of the anvil of the surgical instrument of FIG. 1.

As best seen in FIG. 3, anvil 400 of the present example comprises a head 410 and a shank 420. Head 410 includes a proximal stapling surface 412 that defines a plurality of staple forming pockets 414. Staple forming pockets 414 are arranged in two concentric annular arrays in the present example. Staple forming pockets 414 are configured to deform staples as the staples are driven into staple forming pockets 414. Proximal stapling surface 412 terminates at an inner edge 416, which defines an outer boundary of an annular recess 418 surrounding shank 420. A breakable washer 417 is positioned within annular recess 418 and is configured to provide the operator with a tactile and audible indication that a distal firing stroke has been completed, in addition to serving as a cutting board, as described in greater detail below.

Shank 420 defines a bore 422 and includes a pair of pivoting latch members 430. Latch members 430 are positioned within bore 422 such that distal ends 434 are positioned at the proximal ends of lateral openings 424, which are formed through the sidewall of shank 420. Latch members 430 thus act as retaining clips. This allows anvil 400 to be removably secured to an actuatable closure member in the form of a trocar 330 of stapling head 300, as will be described in greater detail below. Shank 420 of anvil 400 and trocar 330 of stapling head 300 thus cooperate with one another as coupling members.

Figure 4:
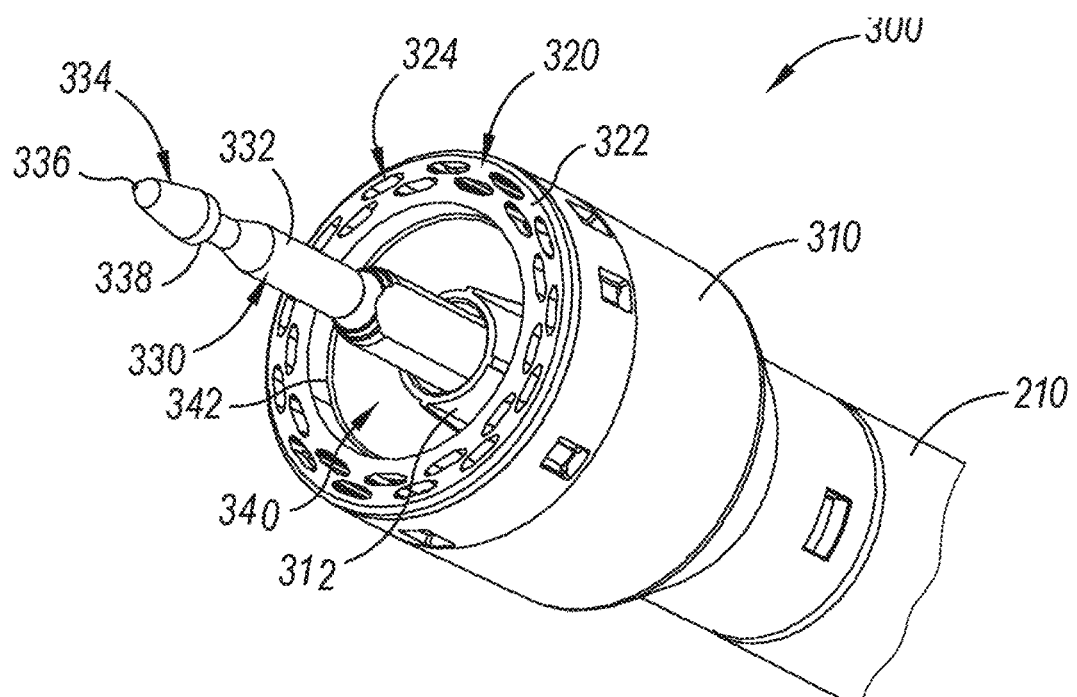
FIG. 4 depicts a perspective view of the stapling head of the surgical instrument of FIG. 1.
Figure 5:
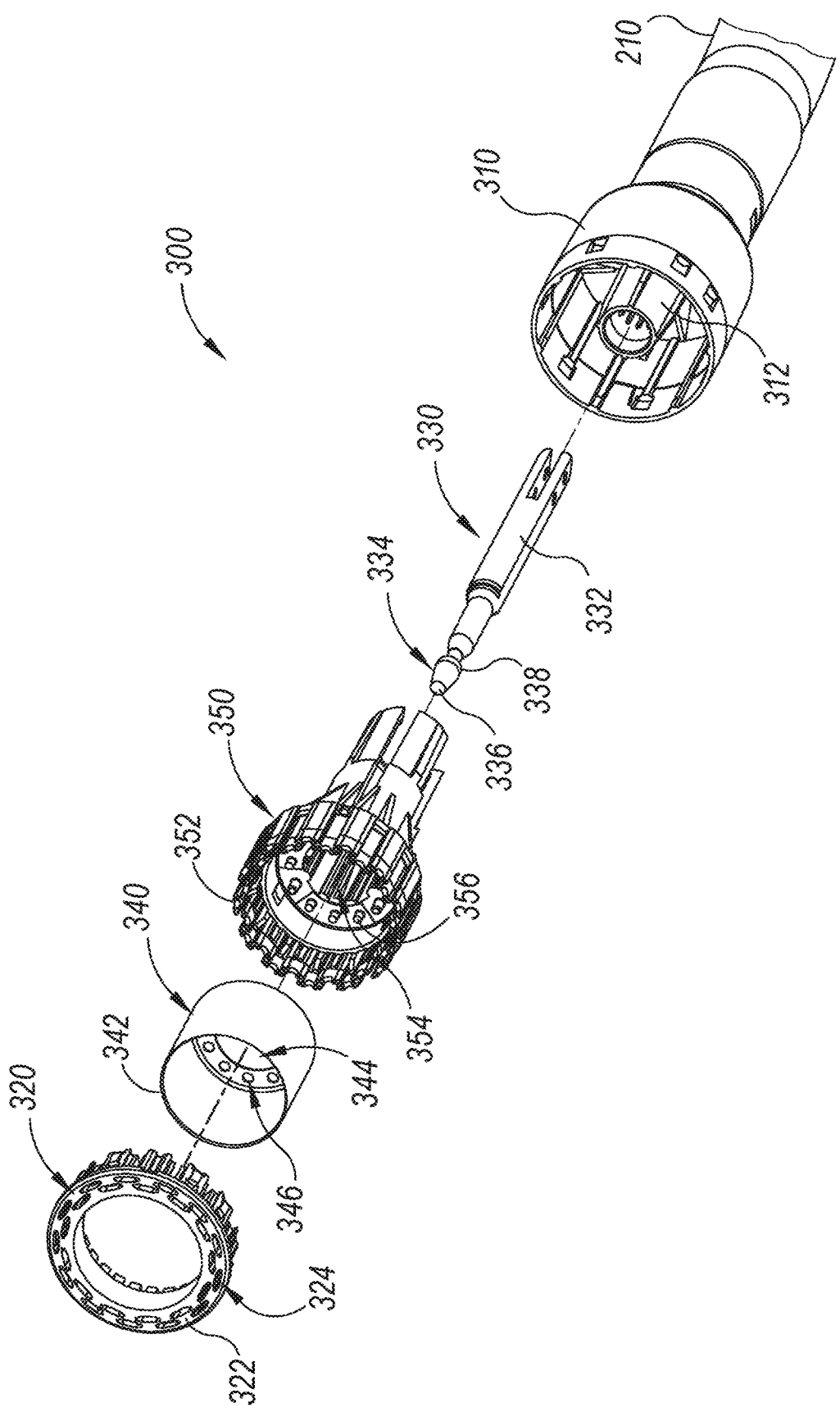
FIG. 5 depicts an exploded perspective view of the stapling head of FIG. 4.

As best seen in FIGS. 4 and 5, stapling head 300 of the present example is coupled to a distal end of shaft 200 and comprises a tubular body member 310 and a staple driver member 350 slidably housed therein. Body member 310 includes a distally extending cylindraceous inner core member 312 positioned coaxially therein. Body member 310 is fixedly secured to an outer sheath 210 of shaft 200, and body member 310 and outer sheath 210 thus serve together as a mechanical ground for stapling head 300.

Trocar 330 is positioned coaxially within inner core member 312 of body member 310. As described in greater detail below, trocar 330 is operable to translate distally and proximally relative to body member 310 in response to rotation of knob 130 relative to casing 110 of handle portion 100. Trocar 330 comprises a shaft 332 and a head 334. Head 334 includes a pointed tip 336 and a radially inwardly extending proximal surface 338. Head 334 and the distal portion of shaft 332 are configured for insertion into bore 422 of anvil 400. Proximal surface 338 and latch shelves 436 have complementary positions and configurations such that latch shelves 436 engage proximal surface 338 when shank 420 of anvil 400 is fully seated on trocar 330. Anvil 400 is thus secured to trocar 330 through a snap fit provided by latch members 430.

Staple driver member 350 is operable to actuate longitudinally within body member 310 in response to activation of motor 160 as described in greater detail below. As shown best in FIG. 5, staple driver member 350 of the present example includes two distally presented concentric annular arrays of staple drivers 352. Staple drivers 352 are arranged to correspond with the arrangement of staple forming pockets 414 of anvil 400. Thus, each staple driver 352 is configured to drive a corresponding staple distally into a corresponding staple forming pocket 414 when stapling head 300 is actuated (or "fired"). Staple driver member 350 also defines a bore 354 that is configured to coaxially and slidably receive core member 312 of body member 310. An annular array of studs 356 project distally from a distally presented surface surrounding bore 354.

A cylindraceous knife member 340 is coaxially positioned within a distally-opening central recess of staple driver member 350 that communicates with bore 354. Knife member 340 includes a distally presented, sharp circular cutting edge 342. Knife member 340 is sized such that knife member 340 defines an outer diameter that is just smaller than the diameter defined by the radially inner-most surfaces of the inner annular array of staple drivers 352. Knife member 340 also defines a central opening that is configured to coaxially receive core member 312 of body member 310. An annular array of openings 346 formed in knife member 340 is configured to mate with the annular array of studs 356 of staple driver member 350, such that knife member 340 is fixedly secured to staple driver member 350 via studs 356 and openings 346.

An annular deck member 320 is fixedly secured to a distal end of body member 310. Deck member 320 includes a distally presented stapling surface in the form of a deck surface 322 having two concentric annular arrays of staple openings 324. Staple openings 324 are arranged to align with the arrangement of staple drivers 352 of staple driver member 350 and staple forming pockets 414 of anvil 400 described above. Each staple opening 324 is configured to slidably receive and provide a pathway for a corresponding staple driver 352 to drive a corresponding staple distally through deck member 320 and into a corresponding staple forming pocket 414 when stapling head 300 is actuated. As best seen in FIG. 5, deck member 320 has a central opening that defines an inner diameter that is just slightly larger than the outer diameter defined by knife member 340. Deck member 320 is thus configured to permit knife member 340 to translate longitudinally through the central opening concurrently with longitudinal translation of staple driver member 350. In particular, knife member 340 is configured to actuate relative to deck member 340 between a proximal retracted position and a distal extended position, where cutting edge 342 is proximal to deck surface 322 in the proximal retracted position and distal to deck surface 322 in the distal extended position.

Figure 6:
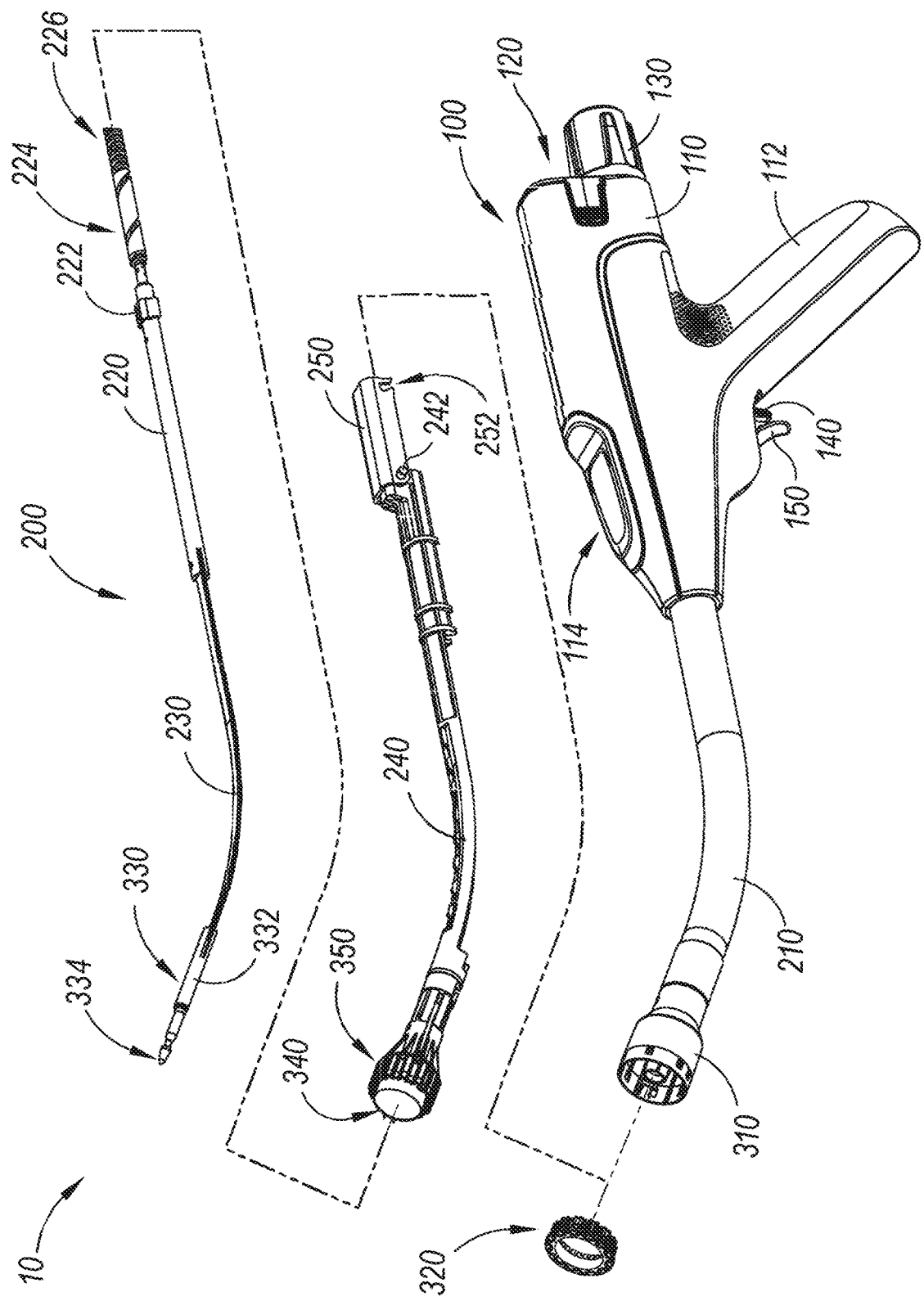
FIG. 6 depicts an exploded perspective view of the surgical instrument of FIG. 1, with portions of the shaft shown separated from each other.

FIG. 6 shows various components of shaft 200, which operatively couple components of stapling head 300 with components of handle 100. In particular, and as noted above, shaft 200 includes an outer sheath 210 that extends between handle 100 and body member 310 and includes a medial portion that extends along a curved path.

Shaft 200 further includes a trocar actuation rod 220 having a proximal end operatively coupled with rotatable knob 130 and a distal end coupled with a flexible trocar actuation band assembly 230, the assembly of which is slidably housed within outer sheath 210. The distal end of trocar actuation band assembly 230 is fixedly secured to the proximal end of trocar shaft 332, such that trocar 330 will translate longitudinally relative to outer sheath 210 in response to translation of trocar actuation band assembly 230 and trocar actuation rod 220 relative to outer sheath 210, which occurs in response to rotation of rotatable knob 130. A clip 222 is fixedly secured to trocar actuation rod 220 and is configured to cooperate with complementary features within handle portion 100 to prevent trocar actuation rod 220 from rotating within handle portion 100 while still permitting trocar actuation rod 220 to translate longitudinally within handle portion 100. Trocar actuation rod 220 further includes a section of coarse helical threading 224 and a section of fine helical threading 226 proximal to coarse helical threading 224, which are configured to control a rate of longitudinal advancement of trocar actuation rod 220, as described in greater detail below.

Shaft 200 further includes a stapling head driver 240 that is slidably housed within outer sheath 210 and about the combination of trocar actuation rod 220 and trocar actuation band assembly 230. Stapling head driver 240 includes a distal end that is fixedly secured to the proximal end of staple driver member 350, a proximal end secured to a drive bracket 250 via a pin 242, and a flexible section disposed therebetween. It should therefore be understood that staple driver member 350 will translate longitudinally relative to outer sheath 210 in response to translation of stapling head driver 240 and drive bracket 250 relative to outer sheath 210.

As shown in FIG. 1, handle portion 100 includes a casing 110 having a lower portion that defines an obliquely oriented pistol grip 112 and an upper portion that supports a user interface feature 114 and releasably receives a battery pack 120, as described in greater detail below. Handle portion 100 further includes several features that are operable to actuate anvil 400 and stapling head 300. In particular, handle portion 100 includes a rotatable knob 130, a safety trigger 140, a firing trigger 150, a motor 160, and a motor activation module 180. Knob 130 is coupled with trocar actuation rod 220 via a nut (not shown), such that coarse helical threading 224 will selectively engage a thread engagement feature within the interior of the nut; and such that fine helical threading 226 will selectively engage a thread engagement feature within the interior of knob 130. These complementary structures are configured such that trocar actuation rod 220 will first translate proximally at a relatively slow rate, and then translate proximally at a relatively fast rate, in response to rotation of knob 130.

It should be understood that when anvil 400 is coupled with trocar 330, rotation of knob 130 will provide corresponding translation of anvil 400 relative to stapling head 300. It should also be understood that knob 130 may be rotated in a first angular direction (e.g., clockwise) to retract anvil 400 proximally toward stapling head 300; and in a second angular direction (e.g., counterclockwise) to extend anvil 400 distally away from stapling head 300. Knob 130 may thus be used to adjust a gap distance (d) between opposing stapling surfaces 412, 322 of anvil 400 and stapling head 300 until a suitable gap distance has been achieved, for example as shown in FIG. 7C described below.

Firing trigger 150 is operable to activate motor 160 to thereby actuate stapling head 300 to staple and cut tissue clamped between anvil 400 and stapling head 300. Safety trigger 140 is operable to selectively block actuation of firing trigger 150 based on the longitudinal position of anvil 400 in relation to stapling head 300. Handle portion 100 also includes components that are operable to selectively lock out both triggers 140, 150 based on the position of anvil 400 relative to stapling head 300. For instance, safety trigger 140 may be blocked from rotating from an engaged position to a disengaged position until the position of anvil 400 relative to stapling head 300 is within a predefined range. Accordingly, until the anvil position is within the predefined range, actuation of firing trigger 150 is blocked by safety trigger 140, thereby inhibiting firing of stapling head 300.

Firing trigger 150 is operable to actuate a switch of motor activation module 180 (FIG. 1) when firing trigger 150 is pivoted proximally to a fired position. Motor activation module 180 is in communication with battery pack 120 and motor 160, such that motor activation module 180 is configured to provide activation of motor 160 with electrical power from battery pack 120 in response to firing trigger 150 actuating the switch of motor activation module 180. Thus, motor 160 will be activated when firing trigger 150 is pivoted. This activation of motor 160 will actuate stapling head 300 via drive bracket 250, as described in greater detail below.

FIGS. 7A-7E show instrument 10 being used to form an anastomosis 70 between two tubular anatomical structures 20, 40. By way of example only, the tubular anatomical structures 20, 40 may comprise sections of a patient's esophagus, colon, or other portions of the patient's digestive tract, or any other tubular anatomical structures.

Figure 7A:
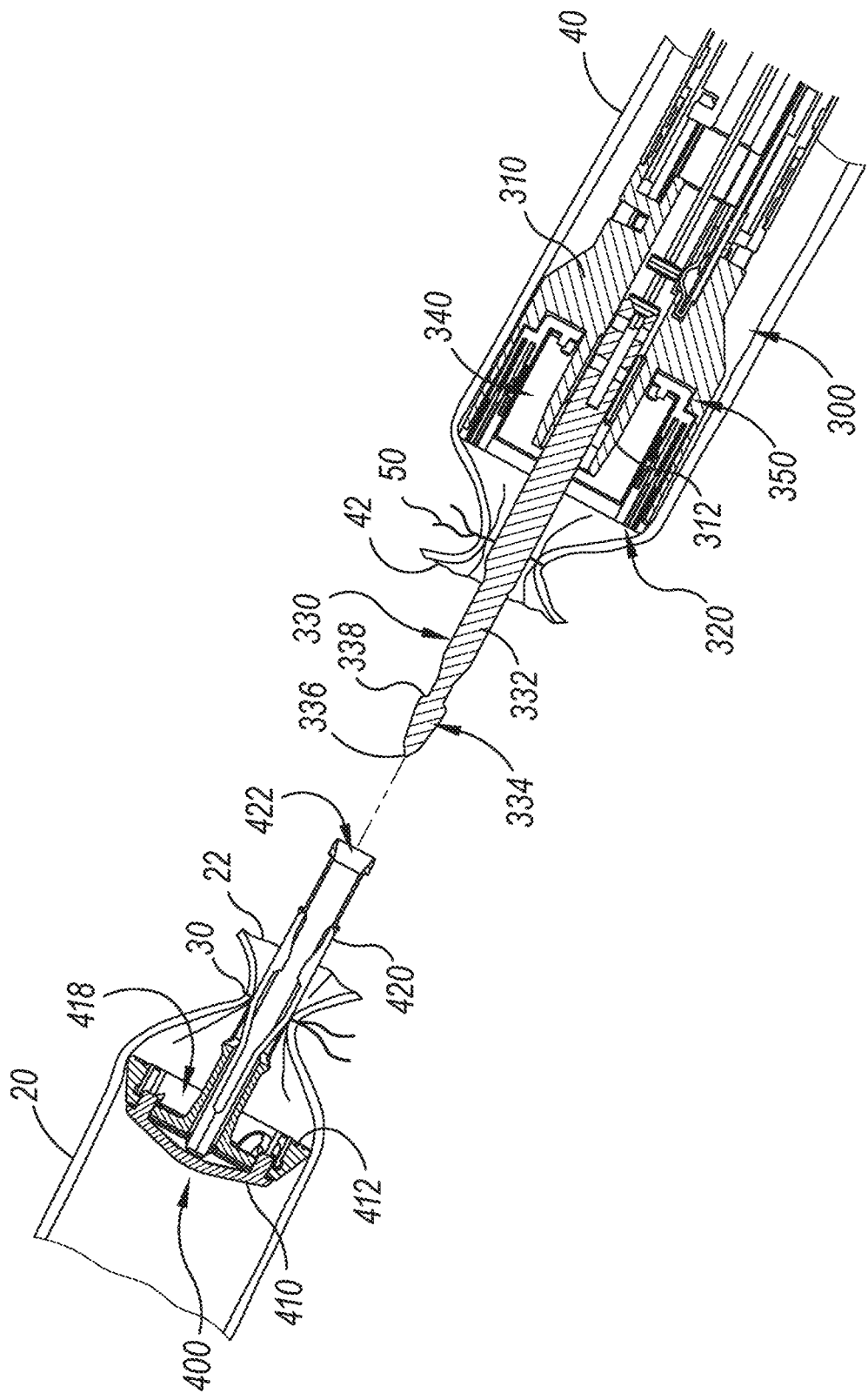
FIG. 7A depicts a cross-sectional side view of the anvil of FIG. 3 positioned within a first section of a digestive tract and the stapling head of FIG. 4 positioned within a separate second section of the digestive tract, with the anvil separated from the stapling head assembly.

As shown in FIG. 7A, anvil 400 is positioned in one tubular anatomical structure 20 and stapling head 300 is positioned in another tubular anatomical structure 40. As shown in FIG. 7A, anvil 400 is positioned in tubular anatomical structure 20 such that shank 420 protrudes from the open severed end 22 of tubular anatomical structure 20. In the present example, a purse-string suture 30 is provided about a mid-region of shank 420 to generally secure the position of anvil 400 in tubular anatomical structure 20. Stapling head 300 is positioned in tubular anatomical structure 40 such that trocar 330 protrudes from the open severed end 42 of tubular anatomical structure 20. A purse-string suture 50 is provided about a mid-region of trocar shaft 332 to generally secure the position of stapling head 300 in tubular anatomical structure 40. Stapling head 300 is then urged distally to ensure that stapling head 300 is fully seated at the distal end of tubular anatomical structure 40.

Figure 7B:
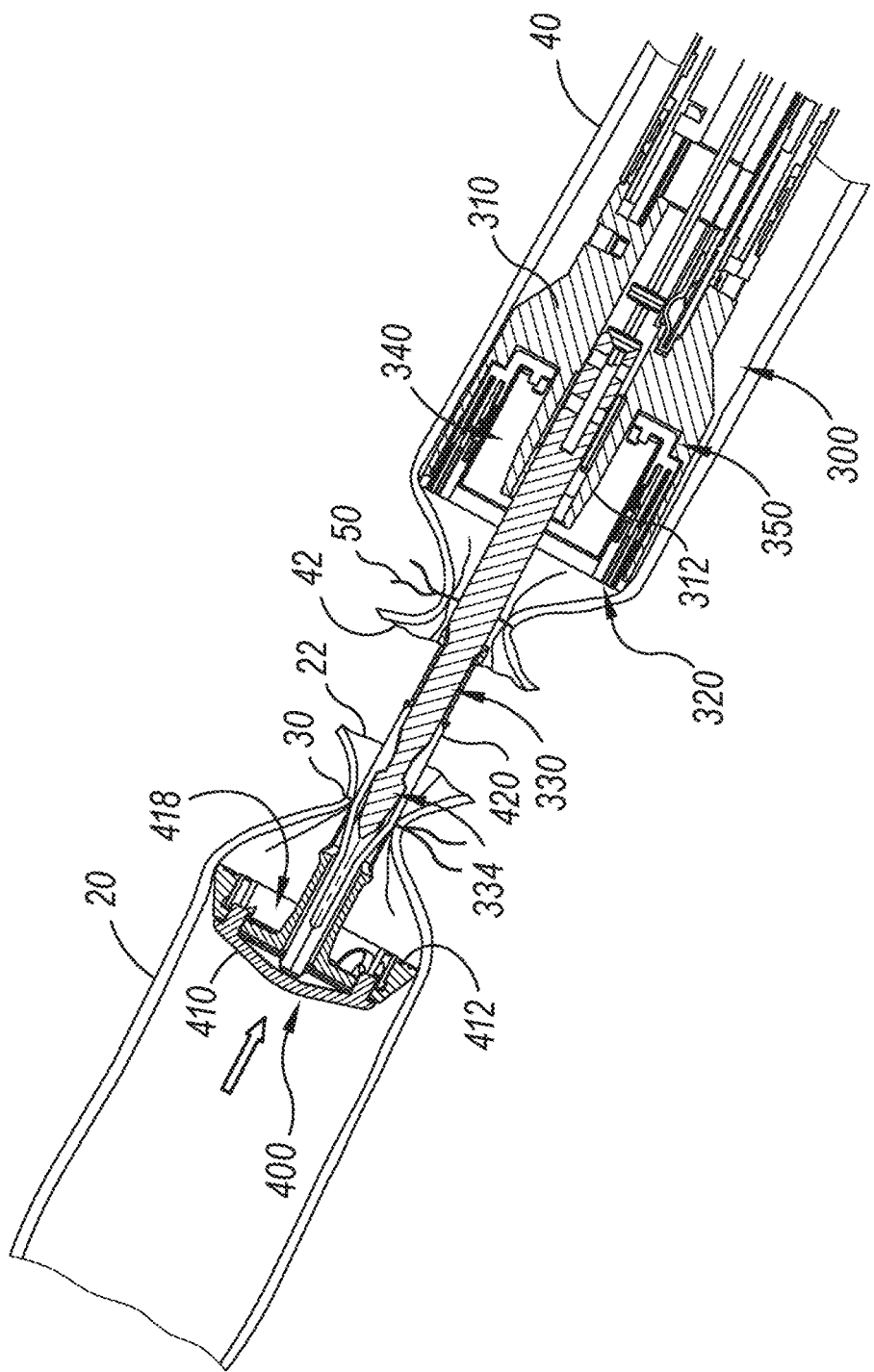
FIG. 7B depicts a cross-sectional side view of the anvil of FIG. 3 positioned within the first section of the digestive tract and the stapling head of FIG. 4 positioned within the separate second section of the digestive tract, with the anvil secured to the stapling head assembly.
Figure 7C:
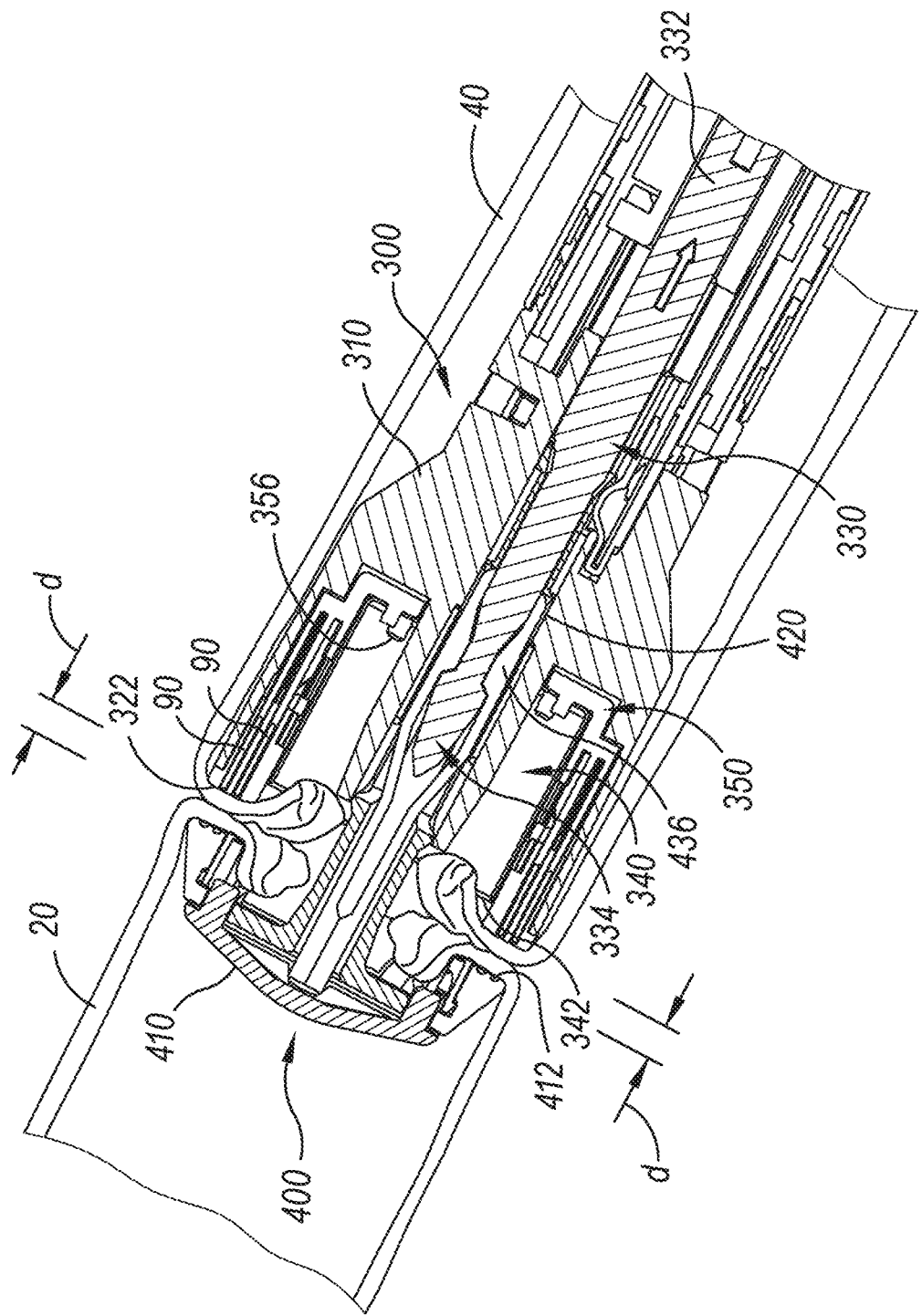
FIG. 7C depicts a cross-sectional side view of the anvil of FIG. 3 positioned within the first section of the digestive tract and the stapling head of FIG. 4 positioned within the separate second section of the digestive tract, with the anvil retracted toward the stapling head to thereby clamp tissue between the anvil and the stapling head assembly.

Next, anvil 400 is secured to trocar 330 by inserting trocar 330 into bore 422 as shown in FIG. 7B. Latch members 430 of anvil 400 engage head 334 of trocar 330, thereby providing a secure fit between anvil 400 and trocar 330. The operator then rotates knob 130 while holding casing 110 stationary via pistol grip 112. This rotation of knob 130 causes trocar 330 and anvil 400 to retract proximally. As shown in FIG. 7C, this proximal retraction of trocar 330 and anvil 400 compresses the tissue of tubular anatomical structures 20, 40 between surfaces 412, 322 of anvil 400 and stapling head 300. As this occurs, the operator may observe the tactile resistance or feedback via knob 130 while turning knob 130, with such tactile resistance or feedback indicating that the tissue is being compressed. As the tissue is being compressed, the operator may visually observe the position of an indicator needle (not shown) within user interface feature 114 of handle portion 100 to determine whether the gap distance (d) between opposing surfaces 412, 322 of anvil 400 and stapling head 300 is appropriate; and make any necessary adjustments via knob 130.

Once the operator has appropriately set the gap distance (d) via knob 130, the operator pivots safety trigger 140 toward pistol grip 112 to enable actuation of firing trigger 150. The operator then pivots firing trigger 150 toward pistol grip 112, thus causing firing trigger 150 to actuate the switch of motor activation module 180 and thereby activate motor 160 to rotate. This rotation of motor 160 causes actuation (or "firing") of stapling head 300 by actuating drive bracket 250 distally to thereby drive knife member 340 and staple driver member 350 distally together, as shown in FIG. 7D.

As knife member 340 translates distally, cutting edge 342 of knife member 340 cuts excess tissue that is positioned within annular recess 418 of anvil 400 and the interior of knife member 340. Additionally, washer 417 positioned within annular recess 418 of anvil 400 is broken by knife member 340 when the knife member 340 completes a full distal range of motion from the position shown in FIG. 7C to the position shown in FIG. 7D. It should be understood that washer 417 may also serve as a cutting board for knife member 340 to assist in cutting of tissue.

Figure 7D:
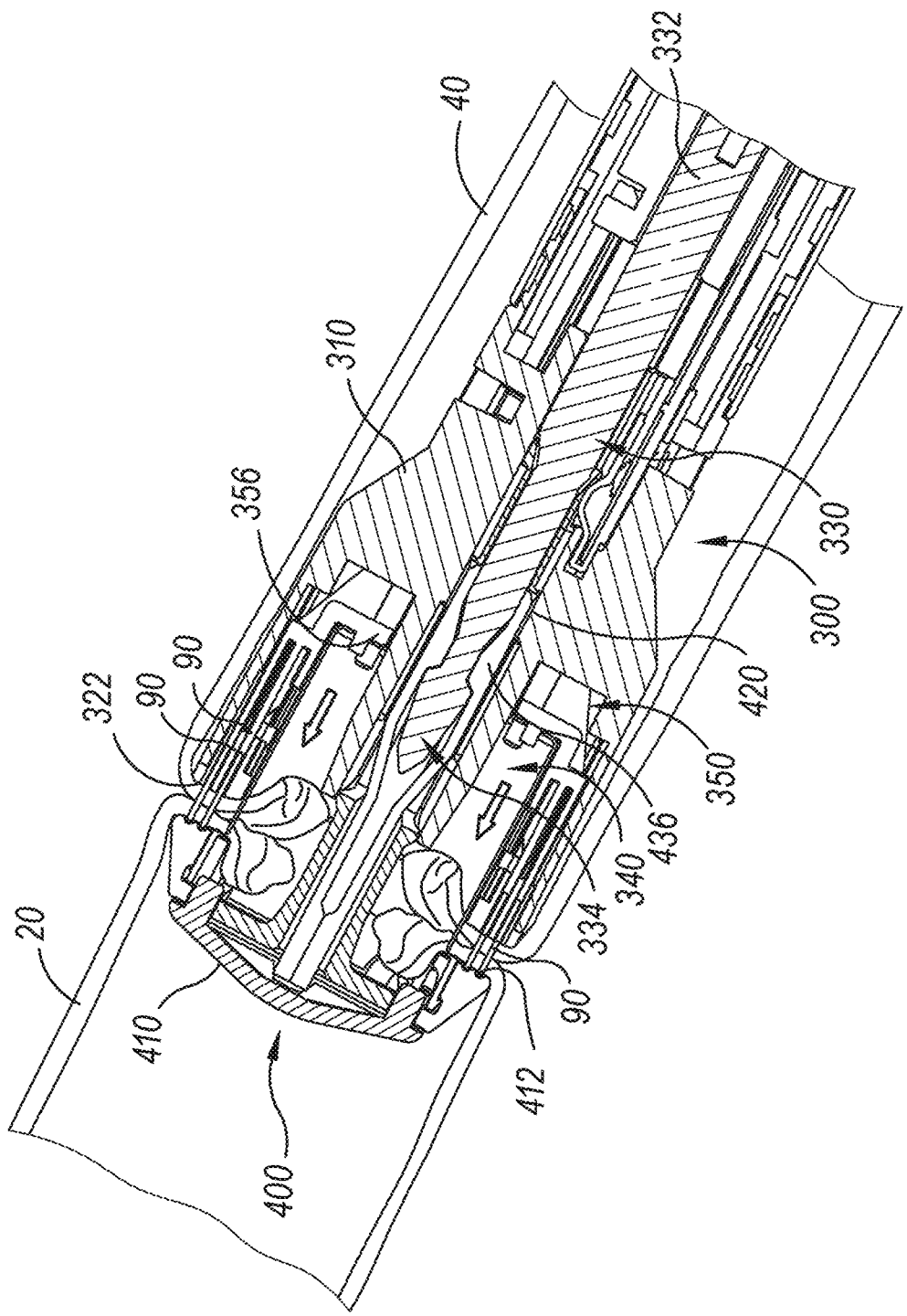
FIG. 7D depicts a cross-sectional side view of the anvil of FIG. 3 positioned within the first section of the digestive tract and the stapling head of FIG. 4 positioned within the second section of the digestive tract, with the stapling head actuated to sever and staple the clamped tissue and thereby joining the first and second sections of the digestive tract.

As staple driver member 350 translates distally from the position shown in FIG. 7C to the position shown in FIG. 7D, staple driver member 350 drives staples 90 through the tissue of tubular anatomical structures 20, 40 and into staple forming pockets 414 of anvil 400. Staple forming pockets 414 deform the driven staples 90 into a "B" shape or a three-dimensional shape, for example, such that the formed staples 90 secure the ends of tissue together, thereby coupling tubular anatomical structure 20 with tubular anatomical structure 40.

After the operator has actuated (or "fired") stapling head 300 as shown in FIG. 7D, the operator rotates knob 130 to drive anvil 400 distally away from stapling head 300, thereby increasing the gap distance (d) to facilitate release of the tissue between surfaces 412, 322. The operator then removes instrument 10 from the patient, with anvil 400 still secured to trocar.

Figure 7E:
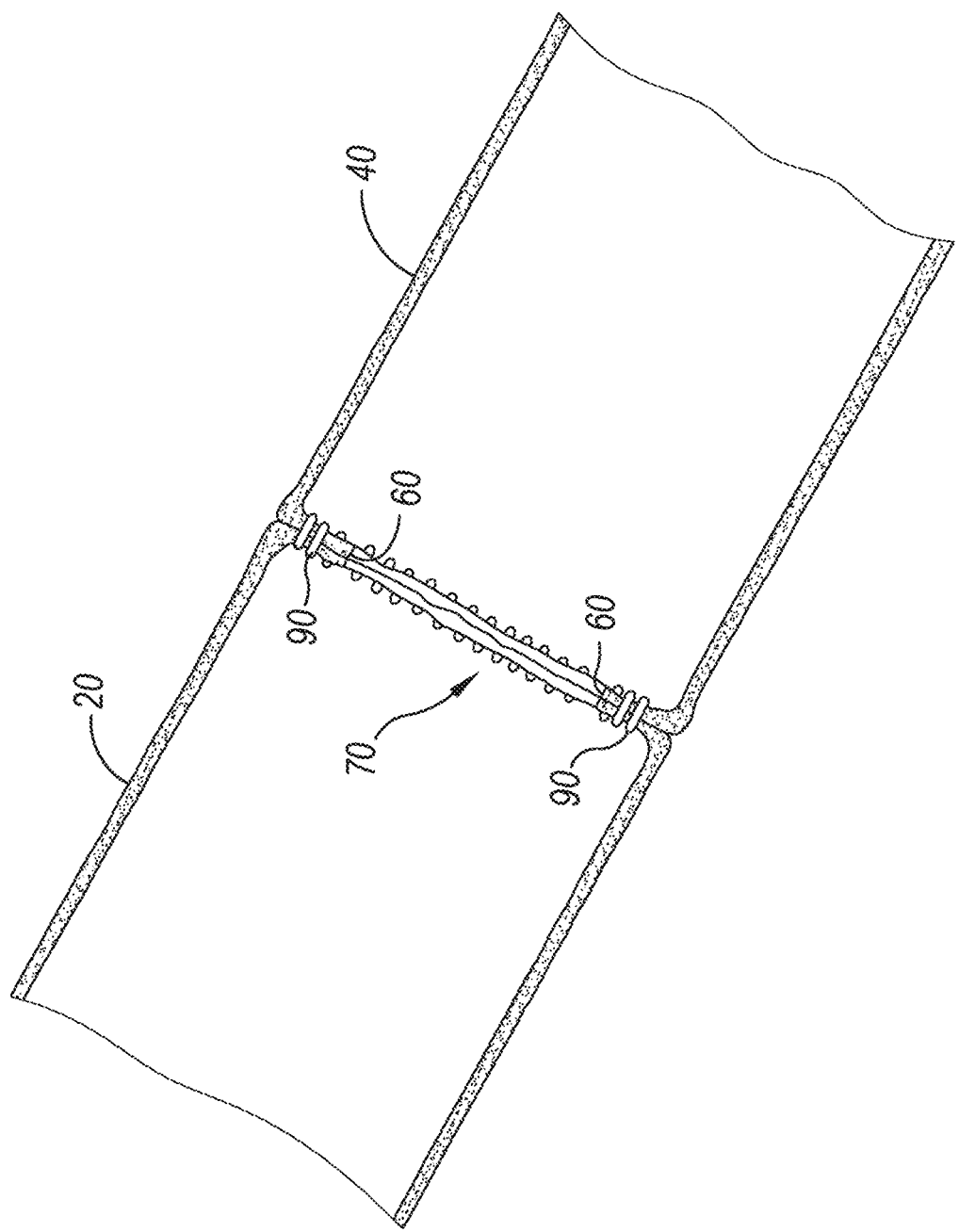
FIG. 7E depicts a cross-sectional side view of the first and second sections of the digestive tract of FIG. 7A joined together at an end-to-end anastomosis formed with the circular stapler of FIG. 1.

With instrument 10 removed, the tubular anatomical structures 20, 40 are left secured together by two annular arrays of staples 90 at an anastomosis 70 as shown in FIG. 7E. The inner diameter of the anastomosis 70 is defined by the severed edge 60 left by knife member 340.

Instrument 10 may be further constructed and operable in accordance with any of the teachings of the following references, the disclosures of which are incorporated by reference herein: in U.S. Pat. No. 5,292,053, entitled "Surgical Anastomosis Stapling Instrument," issued Mar. 8, 1994; U.S. Pat. No. 5,333,773, entitled "Surgical Anastomosis Stapling Instrument," issued Aug. 2, 1994; U.S. Pat. No. 5,350,104, entitled "Surgical Anastomosis Stapling Instrument," issued Sep. 27, 1994; and U.S. Pat. No. 5,533,661, entitled "Surgical Anastomosis Stapling Instrument," issued Jul. 9, 1996; U.S. Pat. No. 8,910,847, entitled "Low Cost Anvil Assembly for a Circular Stapler," issued Dec. 16, 2014; U.S. Pub. No. 2015/0083772, entitled "Surgical Stapler with Rotary Cam Drive and Return," published Mar. 26, 2015, now abandoned; U.S. Pat. No. 9,936,949, entitled "Surgical Sta-pling Instrument with Drive Assembly Having Toggle Features," issued Apr. 10, 2018; U.S. Pat. No. 9,907,552, entitled "Control Features for Motorized Surgical Stapling Instrument," issued Mar. 6, 2018; U.S. Pat. No. 9,713,469, entitled "Surgical Stapler with Rotary Cam Drive," issued Jul. 25, 2017; U.S. Pub. No. 2018/0132849, entitled "Staple Forming Pocket Configurations for Circular Surgical Stapler Anvil," published May 17, 2018; and/or U.S. Pat. No. 10,709,452, entitled "Methods and Systems for Performing Circular Stapling," issued Jul. 14, 2020.

Figure 8:
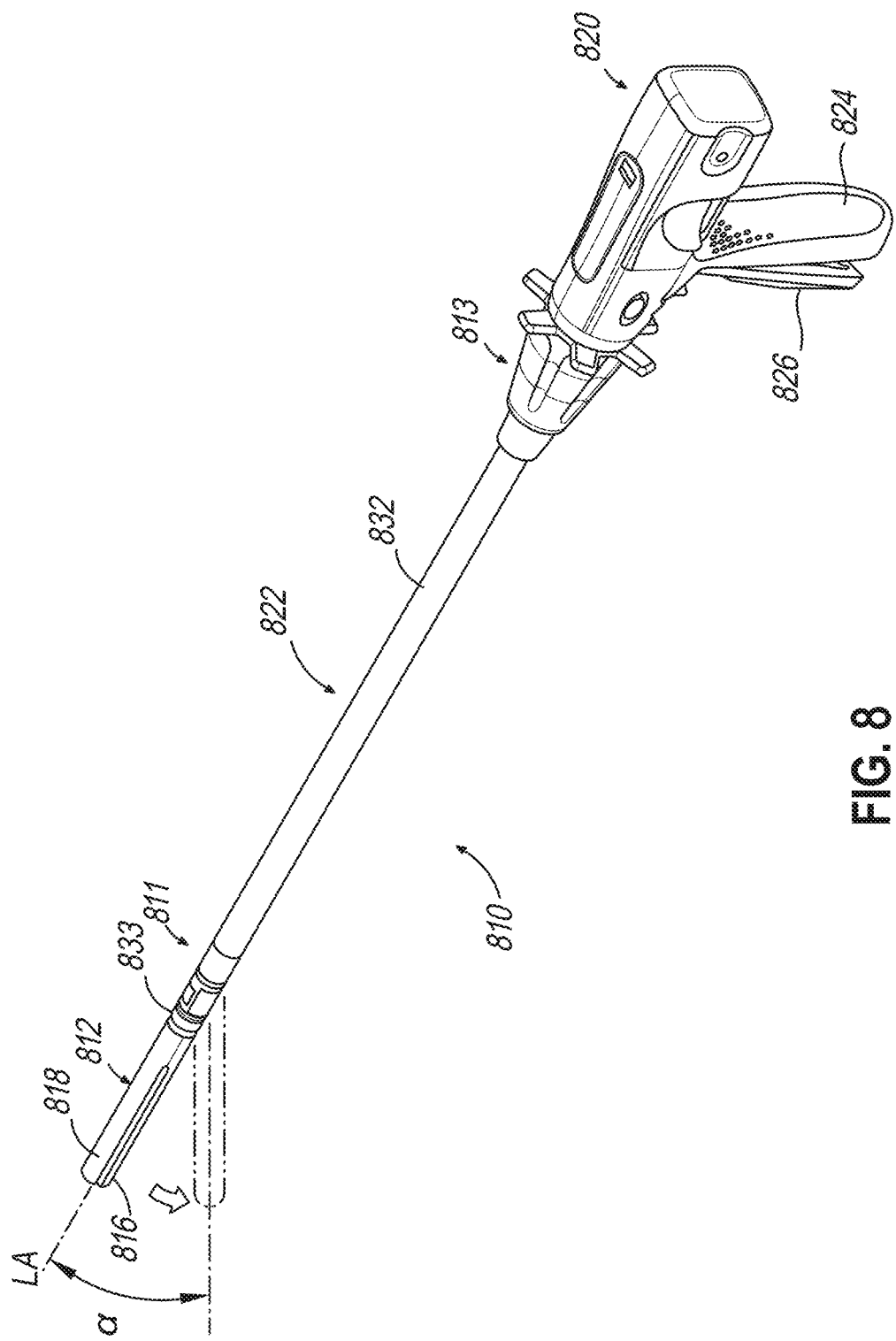
FIG. 8 depicts another example of a surgical instrument configured as a surgical stapler.

FIG. 8 depicts an example of a surgical stapling and severing instrument 800 that is sized for insertion through a trocar cannula or an incision (e.g., thoracotomy, etc.) to a surgical site in a patient for performing a surgical procedure. Instrument 810 of the present example includes an actuator in the form of manually operated handle portion 820, connected to a shaft 822. The shaft 822 distally terminates in an articulation joint 811, which is further coupled with an end effector 812. Once articulation joint 811 and end effector 812 are inserted through the cannula passageway of a trocar, articulation joint 811 may be remotely articulated by an articulation control 813, such that end effector 812 may be deflected from the longitudinal axis (LA) of shaft 822 at a desired angle (a). End effector 812 of the present example includes a lower jaw 816 (also referred to herein as a cartridge jaw) that includes a staple cartridge 837, and an upper jaw 818 in the form of a pivotable anvil jaw.

Unless otherwise described, the term "pivot" (and variations thereof) as used herein encompasses but is not necessarily limited to pivotal movement about a fixed axis. For instance, in some versions, upper jaw 818 may pivot about an axis that is defined by a pin (or similar feature) that slidably translates along an elongate slot or channel as upper jaw 818 moves toward lower jaw 816. Such translation may occur before, during, or after the pivotal motion. It should therefore be understood that such combinations of pivotal and translational movement are encompassed by the term "pivot" and variations thereof as used herein.

Handle portion 820 includes a pistol grip 824 and a closure trigger 826. Closure trigger 826 is pivotable toward pistol grip 824 to cause clamping, or closing, of upper jaw 818 toward lower jaw 816 of end effector 812. Such closing of upper jaw 818 is provided through a closure tube 832 and a closure ring 833, which both longitudinally translate relative to handle portion 820 in response to pivoting of closure trigger 826 relative to pistol grip 824. Closure tube 832 extends along the length of shaft 822; and closure ring 833 is positioned distal to articulation joint 811. Articulation joint 811 is operable to communicate/transmit longitudinal movement from closure tube 832 to closure ring 833.

Handle portion 820 also includes a firing trigger (obstructed in FIG. 8). An elongate member (not shown) longitudinally extends through shaft 822 and communicates a longitudinal firing motion from handle portion 820 to a firing beam in response to actuation of firing trigger. This distal translation of firing beam causes the stapling and severing of clamped tissue in end effector 812. End effector 812 includes a cutting edge to cut through tissue and a staple cartage that may be removably inserted into a channel of the end effector 812 containing staples and staple strivers for driving staples into tissue.

A more detailed description of operation of instruments such as the surgical instrument 800, according to various embodiments, may be found in the following references, the disclosures of which are incorporated by reference herein: U.S. Pat. No. 8,210,411, entitled "Motor-Driven Surgical Instrument," issued Jul. 3, 2012; U.S. Pat. No. 9,186,142, entitled "Surgical Instrument End Effector Articulation Drive with Pinion and Opposing Racks," issued on Nov. 17, 2015; U.S. Pat. No. 9,517,065, entitled "Integrated Tissue Positioning and Jaw Alignment Features for Surgical Stapler," issued Dec. 13, 2016; U.S. Pat. No. 9,622,746, entitled "Distal Tip Features for End Effector of Surgical Instrument," issued Apr. 18, 2017; U.S. Pat. No. 9,717,497, entitled "Lockout Feature for Movable Cutting Member of Surgical Instrument," issued Aug. 1, 2017; U.S. Pat. No. 9,795,379, entitled "Surgical Instrument with Multi-Diameter Shaft," issued Oct. 24, 2017; U.S. Pat. No. 9,808,248, entitled "Installation Features for Surgical Instrument End Effector Cartridge," issued Nov. 7, 2017; U.S. Pat. No. 9,839,421, entitled "Jaw Closure Feature for End Effector of Surgical Instrument," issued Dec. 12, 2017; and/or U.S. Pat. No. 10,092,292, entitled "Staple Forming Features for Surgical Stapling Instrument," issued Oct. 9, 2018.

Figure 9:
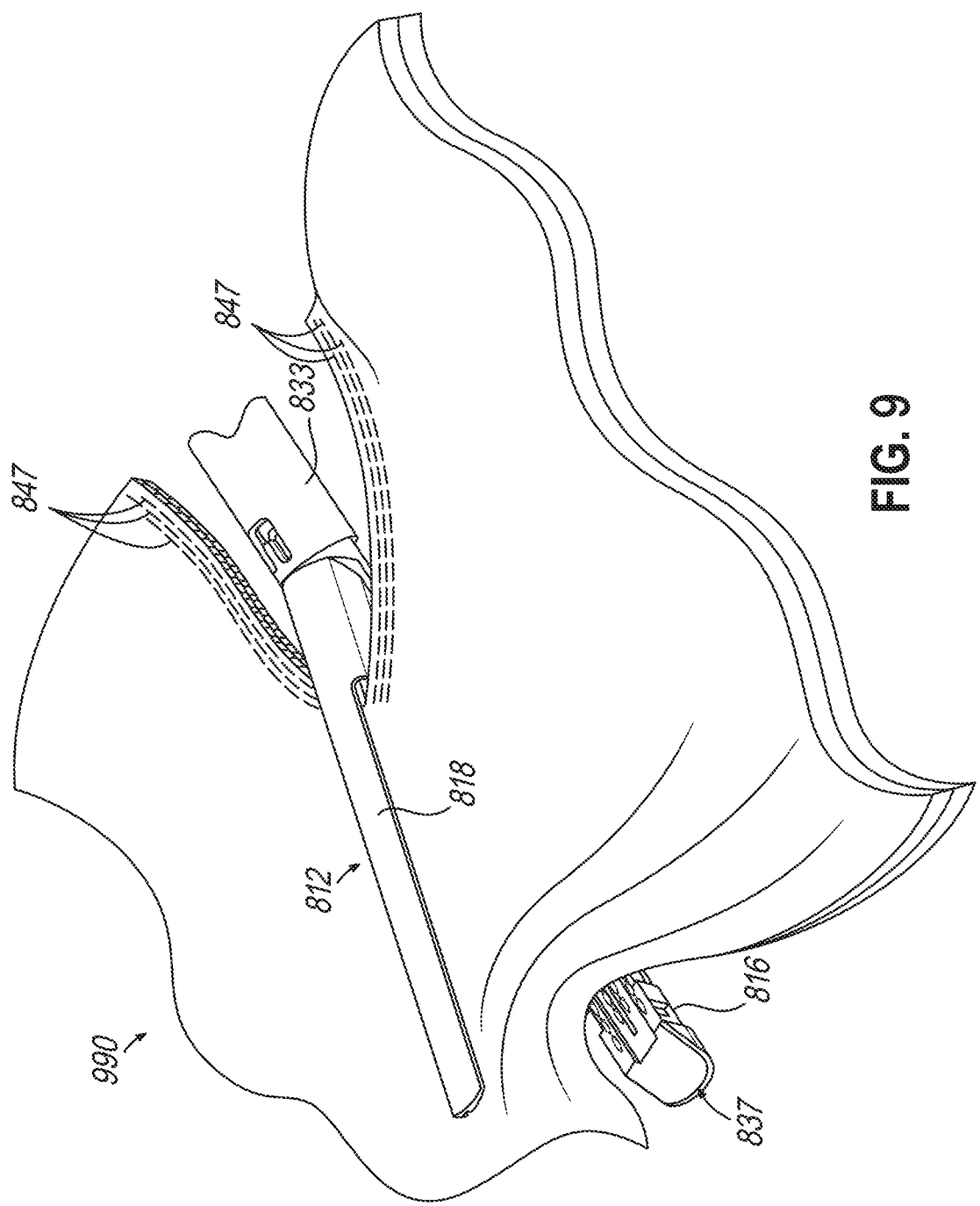
FIG. 9 depicts an end effector of the surgical instrument of FIG. 8 having been actuated through a single firing stroke through tissue.

FIG. 9 shows end effector 812 having been actuated through a single firing stroke through tissue 990. Cutting edge of the end effector 812 has cut through tissue 990, while staple drivers have driven three alternating rows of staples 847 through tissue 990 on each side of the cut line produced by the cutting edge of the end effector 812. After the first firing stroke is complete, end effector 812 may be withdrawn from the patient, spent staple cartridge 837 may be replaced with a new staple cartridge 837, and end effector 812 may then again inserted into the patient to reach the stapling site for further cutting and stapling. This process may be repeated until the desired quantity and pattern of firing strokes across the tissue 990 has been completed.

Figure 10:
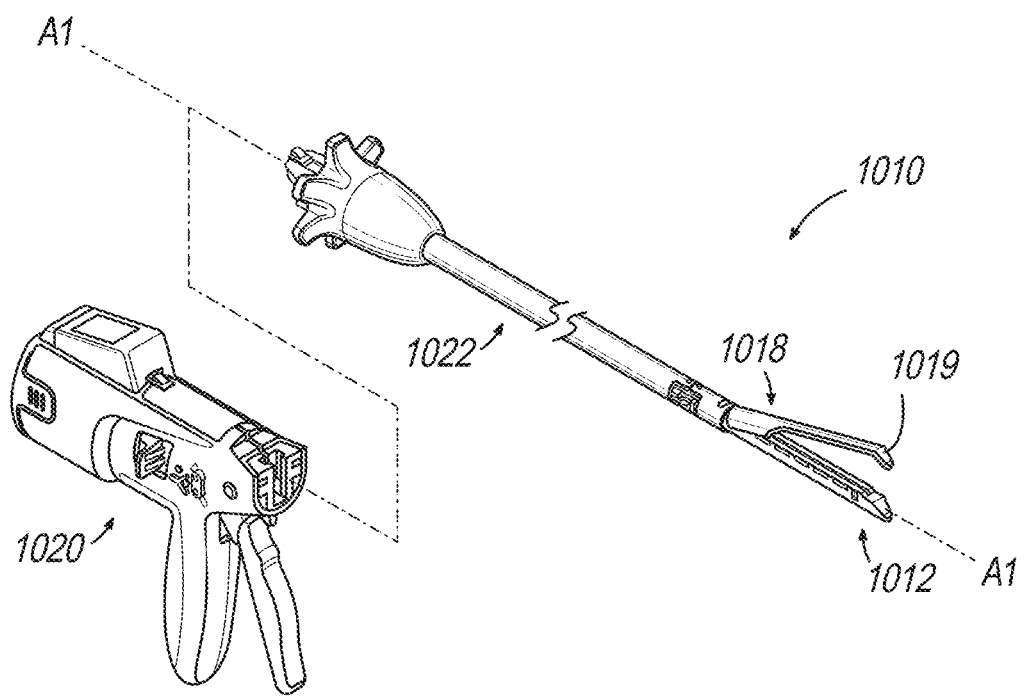
FIG. 10 depicts an example of a surgical instrument configured such that the surgical instrument is attachable to a robotic device, such as a robotic arm.

FIG. 10 shows an example of a surgical instrument 1010 configured such that the surgical instrument is attachable to a robotic system, such as a robotic arm. Instrument 1010 includes an actuator such as a manually operated handle portion 1020 and a shaft 1022. Instrument 1010 has a modular configuration such that shaft 1022 is selectively removable from, and attachable to, handle portion 1020.

Instrument 1010 is configured similarly to instrument 10 or instrument 810 such that the operability and use of instrument 1010 is the same as described above for instrument 10 or instrument 810 with the added feature of instrument 1010 being a modular configuration. With its modular configuration, instrument 1010 provides a way to change the end effector. Such a change in the end effector may be made to replace an otherwise worn end effector, or to provide for a different end effector configuration based on the procedure or user preference. In addition to or in lieu of the foregoing, features operable for providing the modular configuration of instrument 1010 may be configured in accordance with at least some of the teachings of U.S. Pat. No. 10,182,813, entitled "Surgical Stapling Instrument with Shaft Release, Powered Firing, and Powered Articulation," issued Jan. 22, 2019, the disclosure of which is incorporated by reference herein. Other suitable components, features, and configurations for providing instrument 1010 with a modular configuration will be apparent to those of ordinary skill in the art in view of the teachings herein. Moreover, it will be understood by those of ordinary skill in the art in view of the teachings herein, that instruments 10, 810 may be modified to incorporate a modular configuration as shown and described with respect to instrument 1010 or other instruments incorporated by reference herein.

In the illustrated example of FIG. 10, instrument 1010 includes a linear end effector 1012 having an upper jaw 1018 that has an angled distal tip 1019. It will be appreciated that end effector 1012 may be used in place of end effector with the stapling head 300 shown in FIG. 1 or end effector 812 shown in FIG. 8, or the end effector with the stapling head 300 shown in FIG. 1 or the end effector 812 shown in FIG. 8 may be used in place of the end effector 1012. In some versions, the end effector 1012 may be integrally formed with shaft 1022 or alternatively may be separately formed and then combined. In some versions, end effector 1012 may be provided for use in robotic systems. In such robotic systems, modular shaft 1022 having end effector 1012 may be attachable to an actuator other than a manually operated handle portion. For example, the modular shaft 1022 having end effector 1012 may be attachable to a portion of the robotic system, such as a robotic arm, for use such that handle portion 1020 is replaced by components of the robotic system. Still in other examples, end effector 1012 may be adapted for use with a robotic system in a manner where end effector 1012 connects with the robotic system without necessarily connecting the entire modular shaft 1022. In view of the teachings herein, other ways to incorporate an end effector having an angled elastically deformable anvil tip into a user operated or robotic operated instrument will be apparent to those of ordinary skill in the art.

II. Shaft Displacement Detection In A Surgical Instrument

Augmented sensing, feedback, and connectivity are desired for both robotic and handheld instruments used in both laparoscopic and open surgeries. The surgical stapling features of the present disclosure seek to enhance preoperative planning, surgical performance, therapeutic support, and training to improve patient outcomes and reduce harm. In particular, the surgical stapling features of the present disclosure augment and enhance a user's, e.g., a surgeon or a robotic system, perception of external force being applied to portions of a surgical instrument by providing feedback to help inform intraoperative decisions based on data sensed and obtained by a shaft deflection detection system.

In some cases, when a surgical instrument is being maneuvered inside a body of a patent, such as during insertion of the surgical instrument into the body of the patient or removal of the surgical instrument from the body of the patient, components of the surgical instrument (e.g., the shaft, the end effector, etc.) may push against tissue or other surrounding anatomy within the body of the patient with sufficient force to potentially cause damage to the patient. For example, in an anastomosis procedure in which a circular stapler is being inserted into or removed from a tubular structure in the body of the patient, such as an intestine, if a component of the circular stapler forcefully pushes against a side of the tubular structure, the circular stapler may rip or puncture the tubular structure. As another example, in a thoracic procedure in which an endoscopic stapler is being inserted to reach a distant surgical site in the body of the patient, the endoscopic stapler may push against a rib, or other anatomical structures (e.g., veins, arteries, nerves, etc. between the ribs) that the surgical instrument needs to maneuver around to reach the distant surgical site, with sufficient force to damage the rib or the other anatomical structures inside the body of the patient.

In some cases, a user operating the surgical instrument may be able to avoid causing damage to the patient by ensuring that the surgical instrument is properly handled inside the body of the patient. For example, an experienced surgeon may feel the resistance that results from a forceful contact of the surgical instrument with the tissue or other anatomy inside the body of the patient, and may ease up on pushing the surgical instrument, and/or reposition the surgical instrument, to avoid causing damage to the patient. In other cases, however, a user may not feel or notice the resistance (or not appreciate the consequences of such resistance) and may thus continue to apply excessive force to the tissue or other anatomy inside the body of the patient, thereby potentially causing harm to the patient. Such situations may occur, for example, when the user is not an experienced surgeon, but is an assistant or a medical student working with the surgeon, for example. Also, in situations in which robotic surgery is performed, the surgical understanding of tissues, forces, and trajectories, such as tactile feedback or feeling, that a surgeon may have had if the surgeon were performing the surgery manually may be missing, and the patient may be harmed if the robotic system is not prevented from applying excessive force to tissue or other anatomy inside the body of the patient.

In embodiments described below, a surgical instrument is equipped with a shaft deflection detection system that may detect movement or displacement of the shaft relative to another component that may be coupled with the shaft of the surgical instrument. The other component may include, for example, an actuator coupled with the shaft of the surgical instrument (e.g., a handle portion coupled with the shaft of the surgical instrument or a robotic arm attached to the shaft of the surgical instrument). Additionally or alternatively, the other component may include an end effector coupled with the shaft of the surgical instrument. The shaft deflection detection system may thus detect shaft displacement caused by external forces experienced by the shaft as the shaft is maneuvered inside the body of the patient. Such external forces may be due to the end effector coupled with the shaft of the surgical instrument meeting a resistance of surrounding tissue or other anatomy as the shaft is maneuvered inside the body of the patient, for example.

The shaft deflection detection system may include one or more springs (e.g., linear or non-linear coil springs) that couple the shaft to the other component at a mechanical junction between the shaft and the other component. The one or more springs may allow controlled movement or deflection of the shaft with respect to the other component that is proportional to external forces experienced by the shaft as the surgical instrument is being maneuvered inside the body of the patient. The shaft deflection detection system may also include one or more sensors that are positioned at the mechanical junction between the shaft and the other component. For example, the one or more sensors may include a plurality of sensors distributed among a plurality of points around the circumference of the shaft at the mechanical junction. The one or more sensors may be configured to sense the movement of the shaft and to generate signals indicative of displacement of the shaft while the shaft is being maneuvered inside the body of the patient.

The signals generated by the one or more sensors may be provided to a controller that may be communicatively coupled with the shaft deflection detection system. The controller may be configured to determine, based on the signals generated by the one or more sensors, magnitudes and directions of external forces experienced by the shaft as the shaft is maneuvered inside the body of the patient. For example, the controller may convert the displacement of the shaft to a force based on the spring force function of the one or more springs that couple the shaft to the other component. In an embodiment in which the one or more sensors comprise a plurality of sensors distributed among a plurality of points around the circumference of the shaft, the controller may determine a vector including magnitudes and directions of the external forces experienced by the shaft at the plurality of points around the circumference of the shaft.

The controller may detect, based on the signals received from the one or more sensors, when excessive force is experienced by the shaft. For example, the controller may determine that excessive force is experienced by the shaft if the external force experienced by the shaft exceeds a predetermined threshold. When excessive force is detected, the controller may generate an alert and may cause the alert to be provided to a user (e.g., a clinician or a robot) operating or otherwise using the surgical instrument. The alert may comprise a haptic feedback signal that may be provided via the handle portion of the surgical instrument, for example. Additionally or alternatively, a visual and/or auditory alert may be provided. The alert may alert the user that the user should ease up on pushing the surgical instrument, and/or reposition the surgical instrument, in order to mitigate the force and avoid harming the patient. In some embodiments, additional information regarding the force may be provided to the user. For example, the controller may determine a magnitude and/or a direction of the force experienced by the shaft and provide a display of the magnitude and/or direction of the force to the user. Such display of the magnitude and/or direction of the force may be provided, for example, on a screen located in an operating room in which the surgical instrument is being used. In an embodiment, the display of the magnitude and/or direction of the force may be overlayed with a visual representation of the shaft being maneuvered inside the anatomical structure in the body of the patient. Such additional information may inform the user of the degree to which the user should ease up and/or a direction in which the user should move the surgical instrument to mitigate the excessive force experienced by the shaft.

In some embodiments, the controller may be further configured to determine a corrective action that may be performed by the user in order to mitigate the excessive force and avoid impediments or snags during insertion and/or removal. In such embodiments, an indication of the corrective action may be provided to the user, for example via a screen or other display either on the handle of the surgical instrument or in the operating room in which the surgical instrument is being used. The indication may inform the user that moving or rotating the surgical instrument in a certain direction is recommended to mitigate the force. The indication may also inform the user of a degree of movement that is recommended to mitigate the force. These and other techniques described herein may reduce chances of causing harm to the patient as the surgical instrument is being maneuvered inside the body of the patient, such as during insertion the surgical instrument into or removal of the surgical instrument from the body of the patient. For example, sensing and communicating the force experienced by the shaft can alert the user of excessive force and help navigate "hang-ups" during insertion and removal. Displaying or otherwise relaying this information to the user helps keep the user informed during the surgical procedure so that the user can ensure that the surgical instrument is properly and appropriately maneuvered to avoid harming the patient during the surgical procedure.

Figure 11:
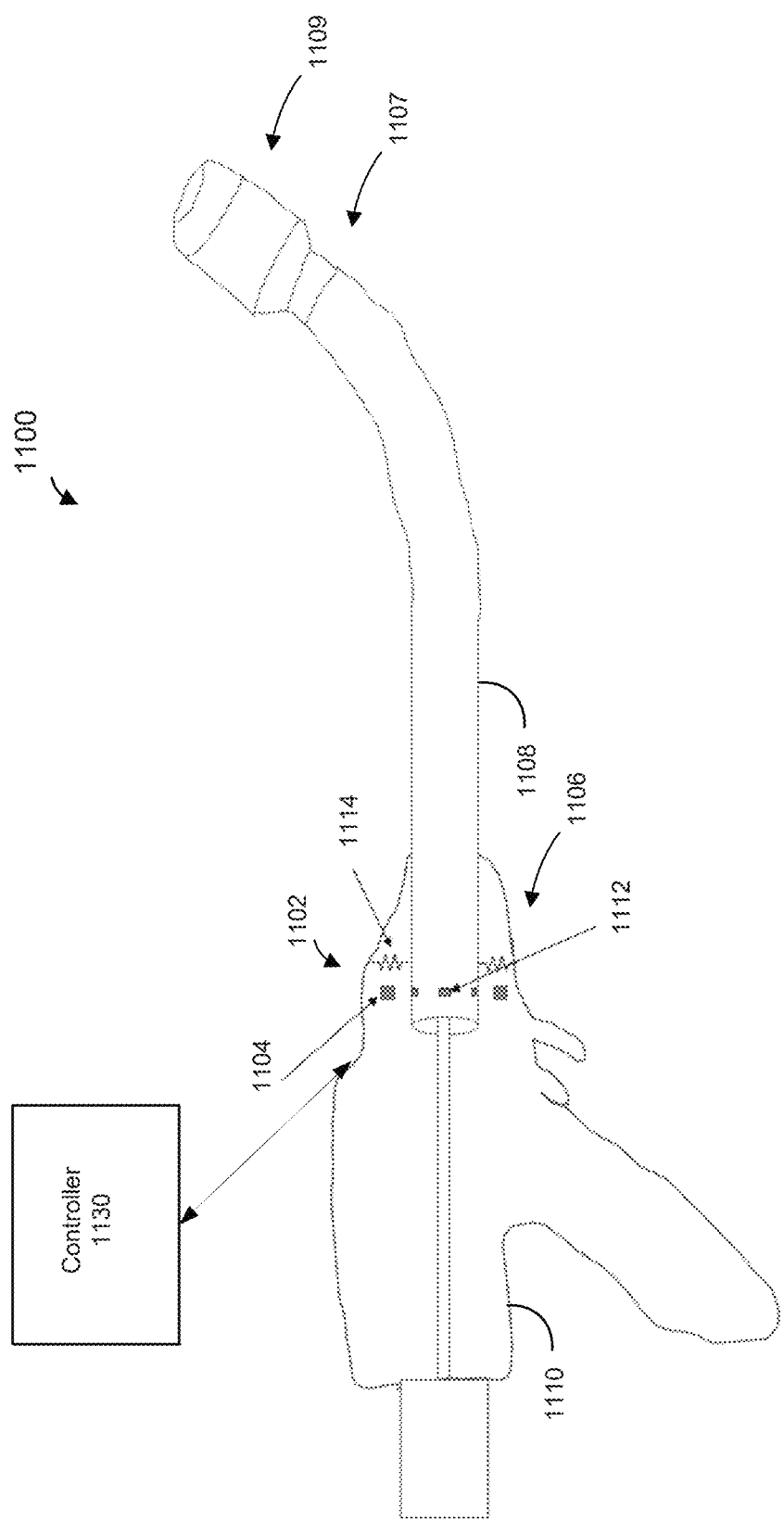
FIG. 11 depicts an example surgical instrument equipped with a shaft deflection detection system.

FIG. 11 depicts an example surgical instrument 1100 equipped with a shaft deflection detection system 1102, according to an embodiment. The surgical instrument 1100 corresponds to the surgical instrument 10, in an embodiment. Although the shaft deflection detection system 1102 is generally described below with reference to the surgical instrument 1100 and the surgical instrument 10, the shaft deflection detection system 1102 may be used with surgical instruments differed from the surgical instrument 1100 or the surgical instrument 10, in some embodiments. For example, the surgical instrument 810 of FIG. 8 may be equipped with a shaft deflection detection system same as or similar to the shaft deflection detection system 1102, in an embodiment. As another example, the surgical instrument 1010 of FIG. 10 may be equipped with a shaft deflection detection system same as or similar to the shaft deflection detection system 1102, in an embodiment.

The surgical instrument 1100 includes a shaft 1108 (e.g., corresponding to the shaft 200 of the instrument 10 of FIG. 1) coupled with an actuator in the form of a manually operated handle portion 1110 (e.g., corresponding to the handle portion 100 of the instrument 10 of FIG. 1) at a proximal end of the shaft 1108. The shaft 1108 may also be coupled with an end effector 1109 (e.g., corresponding to the stapling head 300 of FIG. 1) at a distal end of the shaft 1108. The shaft deflection detection system 1102 includes one or more sensors 1104 positioned at a mechanical junction 1106 between the shaft 1108 and the handle portion 1110 of the surgical instrument 1100. In another example, the shaft 1108 may be coupled with an actuator other than the handle portion 1110 at the mechanical junction 1106. For example, the shaft 1108 may be attached to a component of a robotic system (e.g., an end of a robotic arm) at the mechanical junction 1106.

The one or more sensors 1104 may comprise a plurality (e.g., an array) of sensors distributed among a plurality of points around a circumference of the shaft 1108 at the mechanical junction 1106, for example. The shaft deflection detection system 1102 may additionally include one or more springs 1114 that couple the shaft 1108 to the handle portion 1110 at the mechanical junction 1106. The one or more springs 1114 may be used to bias the shaft 1108 to a nominally centered or neutral position when no load or force is applied to the shaft 1108. The one or more springs 1114 may comprise linear coil springs, for example. The mechanical junction 1106 may be designed such that the shaft 1108 has a degree of flexibility or compliance that allows movement of the shaft 1108 with respect to the handle portion 1110. For example, the mechanical junction 1106 may be made of a suitable material that is sufficiently flexible or compliant to allow movement of the shaft 1108 with respect to the handle portion 1110. Thus, as the shaft 1108 experiences external forces when the shaft or another component (e.g., the end effector 1109) pushes against tissue or other anatomy inside a body of a patient, the shaft 1108 may move relative to the handle portion 1110. The one or more sensors 1104 are configured to measure movement of the shaft 1108 relative to the handle portion 1110 and to generate signals indicative of a force experienced by the shaft 1108 as shaft 1108 is maneuvered inside a body of the patient.

In an example, the sensors 1104 may include four sensors 1104 distributed at 90 degree angles relative to one another around the circumference of the shaft 1108. In this example, the sensors 1104 may be configured to measure movement of the shaft 1108 in the north, south, east, and west directions, for example. In another example, the sensors 1104 may include a suitable numbers of sensors other than four. For example, the sensors 1104 may include a greater number of sensors to provide greater force direction measurement granularity. As just an example, the sensors 1104 may include eight sensors 1104 distributed at 45 degree angles relative to one another around the circumference of the shaft 1108. In another example, the sensors 1104 may include fewer than four sensors, for example to reduce the complexity and cost of the surgical instrument 1100 while still providing useful shaft deflection measurements. As just an example, the sensors 1104 may include two sensors 1104 distributed at a 180 degree angle relative to one another around the circumference of the shaft 1108. In this example, each of the two sensors 1104 may be configured to sense movement of the shaft 1108 in two directions. For example, a first sensor 1104 may be configured to sense movement of the shaft 1108 in the north and south directions and a second sensor 1104 may be configured to sense movement of the shaft 1108 in east and west directions. In other examples, the shaft deflection detection system 1102 may include other suitable numbers and/or other suitable configurations of sensors 1104.

The sensors 1104 may comprise Hall effect sensors or other magnetic sensors positioned on an inner surface of the handle portion 1110 at the mechanical junction 1106, for example. The shaft deflection detection system 1102 may additionally include one or more magnets 1112 positioned on an outer surface of the shaft 1108 at the mechanical junction 1106 at least substantially directly across from the sensors 1104. In another example, the one or more sensors 1104 may be positioned on an outer surface of the shaft 1108 at the mechanical junction 1106 and the one or more magnets 1112 may be positioned on an inner surface of the handle portion 1110 at the mechanical junction 1106 at least substantially directly across from the sensors 1104. The one or more springs 1114 may be positioned between the shaft 1108 and the handle portion 1110 at the mechanical junction 1106 such that movement of the shaft 1108 relative to the handle portion 1110 compresses or decompresses the springs 1114. The springs 1114 may be positioned around the circumference of the shaft 1108 in spaces between sensors 1104, for example. The one or more springs 1114 may comprise linear coil springs characterized by a predetermined spring force function (e.g., a spring constant). In other examples, springs other than linear coil springs and/or non-linear springs may be used. The non-linear springs may be characterized by a known spring function, for example.

In an embodiment, the Hall effect sensors 1104 may comprise a plurality (e.g., an array) of sensors distributed among a plurality of points around the circumference of the handle portion 1110 at the mechanical junction 1106. The magnets 1112 may similarly comprise a plurality (e.g., an array) of magnets distributed among a plurality of points around the circumference of the shaft 1108 at the mechanical junction 1106. In another example, the magnets 1112 may include a single magnet that covers the circumference of the shaft 1108 at the mechanical junction 1106. The Hall effect sensors 1104 may sense magnetic fields generated by the magnets 1112 and generate signals that are proportional to the magnetic field sensed by the sensors 1104. As the shaft 1108 is deflected with respect to the handle 1110 at the mechanical junction 1106 due to external forces experienced along the shaft 1108, the magnetic field sensed by the Hall effect sensors 1104 changes due to a change in distance between the Hall effect sensors 1104 and the magnets 1112. The sensed change in magnetic field may thus be indicative of magnitudes of external forces experienced by the shaft 1108 at the plurality of points around the circumference of the shaft 1108 as the shaft 1108 is maneuvered inside the body of the patient.

The shaft deflection detection system 1102 may include or be communicatively coupled with a controller 1130. The controller 1130 may be located in the handle portion 1110 of the surgical instrument 1100. In another example, the controller 1130 may be implemented at least partially externally to the surgical instrument 1100. For example, the controller 1130 may be implemented at least partially on a processor of a computer that may be located in an operating room in which the surgical instrument 1100 may be used. The controller 1130 may be configured to receive signals generated by the sensors 1104 and detect external forces experienced by the shaft 1108 based on the signals received from the sensors 1104. For example, the controller 1130 may be configured to convert the detected deflection of the shaft 1108 to a magnitude of force experienced by the shaft 1108 based on the predetermined spring force function (e.g., spring constant) of the springs 1114. In an embodiment in which the sensors 1104 comprise a plurality (e.g., an array) of sensors distributed among a plurality of points around the circumference of the shaft 1108, the controller 1130 may be configured to determine a vector of forces experienced along the shaft 1108 at the plurality of points around the circumference of the shaft 1108. The vector may indicate direction and magnitude of the force experienced along the shaft 1108. In this way, the vector may indicate movement of the shaft 1108.

The controller 1130 may detect, based on the determined forces experienced by the shaft 1108 at one or more points around the circumference of the shaft 1108, when the external force experienced by the shaft 1108 is excessive. For example, the controller 1130 may determine that excessive force is experienced by the shaft 1108 if magnitudes of one or more of the determined forces exceed a predetermined threshold. In some embodiments, a plurality of predetermined thresholds may be provided. For example, different thresholds may be defined for different types of tissue and/or other anatomy in the body of the patient. The plurality of thresholds may be stored in a memory included in or coupled to the controller 1130. The controller 1130 may then select an appropriate threshold based on the type of tissue or other anatomy according to a setting provided by a user depending on the surgical procedure, for example.

When excessive force is detected, the controller 1130 may generate an alert and may cause the alert to be provided to the user. The alert may alert the user that the user should ease up on pushing the surgical instrument 1100, and/or should reposition the surgical instrument 1100, in order to mitigate the external force. The alert may comprise a haptic feedback signal that may be provided via the handle portion 1110, for example. Additionally or alternatively, the controller 1130 may be configured to generate and provide a visual and/or auditory alert to the user.

In some embodiments, additional information regarding the external force experienced by the shaft 1108 may be provided to the user. For example, the controller 1130 may determine a magnitude and/or a direction of the external force experienced by the shaft 1108. The magnitude and/or direction of the force may be displayed to the user. The controller 1130 may cause such display to be provided to the user via a screen located on the handle portion 1110 of the surgical instrument 1100 or via a screen or display in an operating room in which the surgical instrument 1100 is being used, for example. In an embodiment, the display of the magnitude and/or direction of the external force may be overlayed with a visual representation of the shaft 1108 being maneuvered inside the anatomical structure in the body of the patient. Such additional information, such as a vector display, may inform the user of the degree to which the user should ease up and/or a direction in which the user should move the surgical instrument 1100 to mitigate the excessive force on the tissue or other anatomical structure (e.g., bone, etc.). In some embodiments, the controller 1130 may be further configured to determine a corrective action that may be performed by the user in order to mitigate the excessive force. The controller 1130 may cause an indication of the corrective action to be provided to the user, for example via the screen or other display on the handle portion 1110 of the surgical instrument 1100 or in the operating room in which the surgical instrument 1100 is being used.

The controller 1130 may include any suitable analog and/or digital circuitry configured to detect external forces experienced by the shaft 1108 and to provide indications to the user of the surgical instrument 1100 when it is determined that excessive force is experienced by the shaft 1108. For example, the controller 1130 may be a fully analogue controller that may include analogue circuitry, such as one or more comparators, that may compare magnitudes of signals received from the sensors 1104 with a threshold, and generate indications of excessive force when the magnitudes of the signals exceed the threshold. The controller 1130 may further include analog indicators that may provide indications of shaft force and/or provide excessive force alerts to the user. In an example, the controller 1130 may include or be coupled to one or several light emitting devices, such as light emitting diodes (LEDs), that may visually indicate points at which excessive force is experienced by the shaft 1108. In an embodiment, respective LEDs may be provided on an outside surface of the handle portion 1110, for example around the circumference of the handle portion 1110, to correspond with the respective ones of the sensors 1104. The controller 1130 may be configured to cause the respective LEDs to light up (e.g., green or red) to indicate whether normal or excessive force is detected based on signals received from the corresponding sensors 1104. In another example, a single light emitting device may be provided, and the controller 1130 may be configured to cause the single light emitting device to, for example, light up (e.g., red) in response to detecting excessive force at any point around the circumference of the shaft 1108. In another embodiment, one or more audio indications may be provided to the user in addition to or instead of the one or more visual indications.

In some implementations, the controller 1130 may be at least partially digital. In some examples, the controller 1130 may be implemented utilizing dedicated hardware, such as one or more of discrete components, an integrated circuit, an application-specific integrated circuit (ASIC), a programmable logic device (PLD), a processor executing firmware instructions, a processor executing software instructions, or any combination thereof. When implemented utilizing a processor executing software or firmware instructions, the software or firmware instructions may be stored in any suitable computer readable memory such as on a magnetic disk, an optical disk, or other storage medium, etc. The software or firmware instructions may include machine readable instructions that, when executed by one or more processors, cause the one or more processors to perform various acts related to determining force experienced by the shaft 1108, determining whether the force or strain is excessive at one or more points around the circumference of the shaft 1108, determining a corrective action that may be taken to mitigate the excessive force, providing indications to a user of the surgical instrument 1100, etc. In some implementations, the controller 1130 may include one or more digital to analog converters (DACs) and one or more analog to digital converters (ADCs) configured to convert signals between analog signals received from the sensors 1104 to digital signals suitable for processing by the digital circuitry of the controller 1130.

In various examples, the alerts and/or corrective action indications may be provided to the user via one or more of i) visual indicators, such as LEDs, that may be provided, for example, on the handle portion 1110 of the surgical instrument 1110, ii) audio indicators and/or iii) a digital screen or other display that may be integrated with the surgical instrument 1100 or communicatively coupled with the surgical instrument 1100. For example, a transmitter may be coupled to the controller 1130 to wirelessly transmit force signals generated based on the signals received from the sensors 1104 to a processor of a computer that may be located, for example, in an operating room in which the surgical instrument 1100 is being used. The processor of the computer may be configured to further process the force signals, for example to identify one or more points around the circumference of the shaft 1108 at which excessive force is experienced by the shaft 1108, determine corrective action that may be performed to mitigate excessive force experienced by the shaft 1108, cause alerts and/or corrective action indications to be displayed on a display coupled to the computer, etc.

It is noted that although the shaft deflection detection system 1102 is generally described herein as including Hall effect sensors 1104 configured to measure movement of the shaft 1108 and generate signals indicative of forces experienced by the shaft 1108, the shaft deflection detection system 1102 may include sensors other than Hall effect sensors and/or may be configured to measure shaft movement quantities other than movement due to external forces experienced by the shaft 1108. For example, the shaft deflection detection system 1102 may be configured to measure strain, pressure, etc. experienced by the shaft 1108, in addition to or instead of measuring forces experienced by the shaft. In some examples, the one or more sensors 1104 may comprise i) one or more encoded strips (e.g., magnet scales) positioned or distributed around the circumference of the shaft 1108 or the handle portion 1110 and configured to move with movement of the shaft 1108 relative to the handle portion 1110 and ii) one or more electromagnetic encoders or read-heads configured to read movement of the encoders or read-heads and provide signals indicative of deflection of the shaft 1108 relative to the handle portion 1110 based on detecting positions of the one or more magnet scales positioned around the circumference of the shaft 1108 or the handle portion 1110. As another example, the one or more sensors 1104 may comprise strain gauge sensors configured to measure strain on the shaft 1108. As yet another example, the one or more sensors 1104 may comprise piezo (e.g., piezoelectric) sensors configured to measure pressure experienced by the shaft 1108. In other examples, other suitable sensors (e.g., resistive sensors, capacitive sensors, etc.) may be used. In some examples, a sensor 1104 and a corresponding spring 1114 may be combined into a single sensor element in the shaft deflection detection system 1102. For example the deflection of the spring may alter a measurable electrical property or other measurable property indicative of movement of the shaft 1108, and such property may be measured by the sensor element to generate a signal indicative of the movement of the shaft 1108.

In some examples, the shaft deflection detection system 1102 may omit the one or more magnets 1112 and/or the one or more springs 1114. For example, mechanisms other than the one or more springs 1114 may be used to bias the shaft 1108 to a nominally centered or neutral position when no load or force is applied to the shaft 1108. In some embodiments, for example, rubber or polymer material may be used instead of the one or more springs 1114. In an example, a rubber or polymer gasket may encircle the shaft 1108 at the mechanical junction 1106 between the shaft 1108 and the handle portion 1110. The rubber or polymer gasket may act as a seal between the shaft 1108 and the handle portion 1110 and may also stretch in any direction when load or force is experienced by the shaft 1108. In other embodiments, other suitable biasing materials and/or mechanisms may be used to bias the shaft 1108 to a nominally centered or neutral position while having the ability to stretch (e.g., compress or decompress) when load or force is experienced by the shaft 1108.

It is also noted that although the deflection detection system 1102 is generally described herein as being positioned at the mechanical junction 1106 (sometimes referred to herein as "first mechanical junction") between the shaft 1108 and the handle portion 1110, in some embodiments, the deflection detection system 1102 may additionally or alternatively include sensors 1104 (and, if needed, other corresponding components such as magnets 1112 and springs 1114 as described herein) at a mechanical junction other than the mechanical junction 1106 between the shaft 1108 and the handle portion 1110. For example, in some embodiments, the shaft deflection detection system 1102 may additionally or alternatively include sensors 1104 (and, if needed, other corresponding components such as magnets 1112 and springs 1114 as described herein) positioned at a mechanical junction 1107 (sometimes referred to herein as "second mechanical junction") between the shaft 1108 and the end effector 1109. The sensors 1104 positioned at the mechanical junction 1107 may detect movement of the shaft 1108 relative to the end effector 1109.

Figure 12:
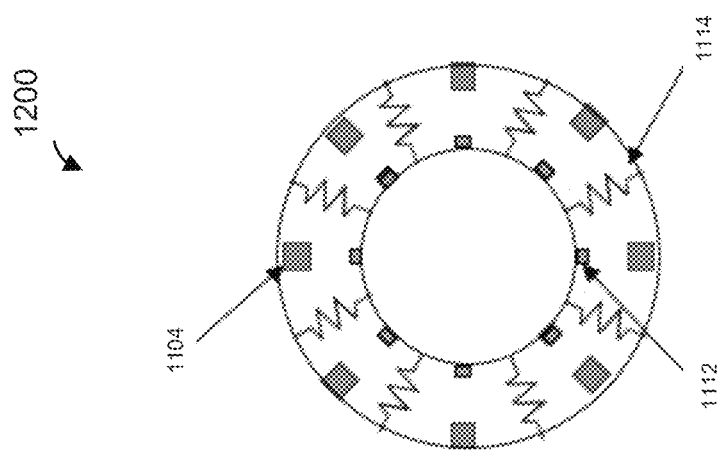
FIG. 12 depicts a cross-section view of the shaft deflection detection system of the surgical instrument of FIG. 11 in a neutral or rest state.

FIG. 12 depicts a cross-section view of the shaft deflection detection system 1102 in which Hall effect sensors are used, according to an embodiment. The shaft deflection detection system 1102 is illustrated in FIG. 12 in a neutral or rest state. The neutral or rest state corresponds to a state in which no external force, or very small external force, is experienced by the shaft 1108 of the surgical instrument 1100. As illustrated in FIG. 12, in the neutral or rest state, the distances between the Hall effect sensors 1104 and the corresponding magnets 1112 of the shaft deflection detection system 1102 may be at least approximately equal. Accordingly, magnitudes of signals generated by different ones of the Hall effect sensors 1104 may be approximately equal to each other. In some embodiments, the controller 1130 may be calibrated to the neutral state of the shaft deflection detection system 1102. For example, the controller 1130 may be configured to measure, and store in a memory, magnitudes of signals received from the sensors 1104 when the shaft deflection detection system 1102 is in the neutral state.

Figure 13:
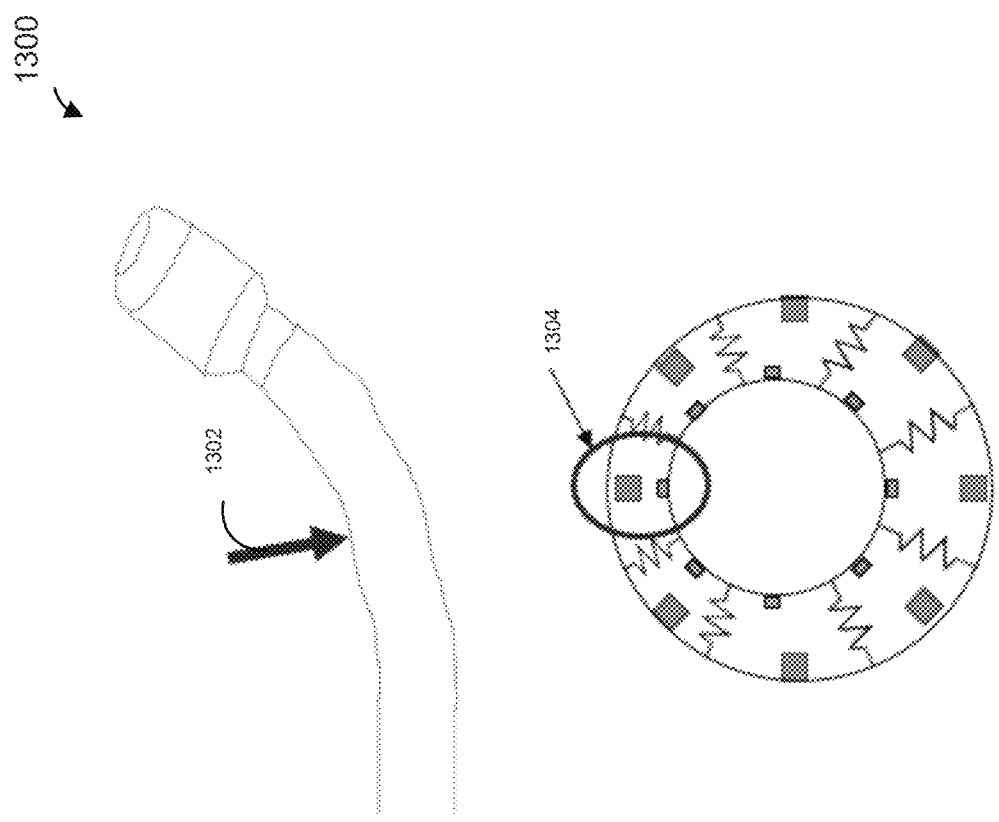
FIG. 13 depicts a cross-section view of the shaft deflection detection system of the surgical instrument of FIG. 11 in a state in which an external force is experienced by the shaft of the surgical instrument.

FIG. 13 depicts a cross-section view of the shaft deflection detection system 1102 in a state in which an external force 1302 is experienced by the shaft 1108 of the surgical instrument 1100, according to an embodiment. The external force 1302 may be due, for example, to the shaft 1108 pushing against tissue or other substance (e.g., bone, rib, etc.) inside of a body a patient, such as during insertion or removal of the surgical instrument 1100 into or from the body of the patient (e.g., into or form a tubular structure, such as an intestine, in the body of the patient). The force 1302 causes deflection of the shaft 1108 relative to the handle portion 1110 of the surgical instrument 1100. Accordingly, distances between Hall effect sensors 1104 and corresponding magnets 1112 change with the movement of the shaft 1108. For example, as illustrated at a point 1304 in FIG. 13, distances between Hall effect sensors 1104 and corresponding magnets 1112 at or near the point(s) around the circumference of the shaft 1108 at which the external force 1302 is exerted along the shaft 1108 decrease as the magnets 1112 positioned on the shaft 11108 are pushed towards the corresponding sensors 1104 positioned on the handle portion 1110. Further, distances between one or more sensors 1104 that are farther away from (e.g., across from) the point(s) around the circumference of the shaft 1108 at which the external force 1302 is exerted along the shaft 1108 increase as the magnets 1112 positioned on the shaft 11108 are pushed farther away from the corresponding sensors 1104 positioned on the handle portion 1110. The changing distances between the sensors 1104 and the magnets 1112 result in corresponding changes of magnetic fields sensed by the sensors 1104, thereby changing the magnitudes of the signals generated by the sensors 1104.

The controller 1130 may thus detect the changes in distance between the Hall effect sensors 1104 and the corresponding magnets 1112, for example by comparing the distances to the corresponding distances measured in the neutral state of the shaft deflection detection system 1102. In an example, the controller 1130 may convert the deflection distances indicated by the signals received from the sensors 1104 to respective forces based on the predetermined spring force functions (e.g., spring constants) of the springs 1114. For example, the force experienced by the shaft 1108 at a particular point around the circumference may be determined by dividing the change in distance between the sensor 1104 at or closest to the particular point on the circumference of the handle portion 1110 and the corresponding sensor 1104 on the shaft 1108. The controller 1130 may further be configured to determine whether the force experienced by the shaft 1108 is excessive. For example, the controller 1130 may be configured to determine whether the force is excessive based on a comparison of the determined force and a predetermined threshold.

In an embodiment, if the controller 1130 determines that the force at one or more points around the circumference of the shaft 1108 exceeds a predetermined threshold, the controller 1130 may generate an alert and/or determine a corrective action, and may provide the alert and/or the determined corrective action to the user of the surgical instrument 1100. The user may thus ease up on pushing the surgical instrument 1100 to avoid causing damage to the patient. The user may also perform the corrective action, for example by shifting the surgical instrument 1100 in a direction determined by the controller 1130, rotating the instrument 1100 as determined by the controller 1130, etc. The user may thus ensure safe maneuvering of the surgical instrument 1100 during a surgical procedure, such as during insertion or removal of the instrument 1100 into or from a tubular structure (e.g., intestine) inside the body of the patient. Accordingly, the user may ensure that components of the surgical instrument 1100 do not, for example, rupture the tubular structure inside the body of the patient during the surgical procedure.

Figure 14A:
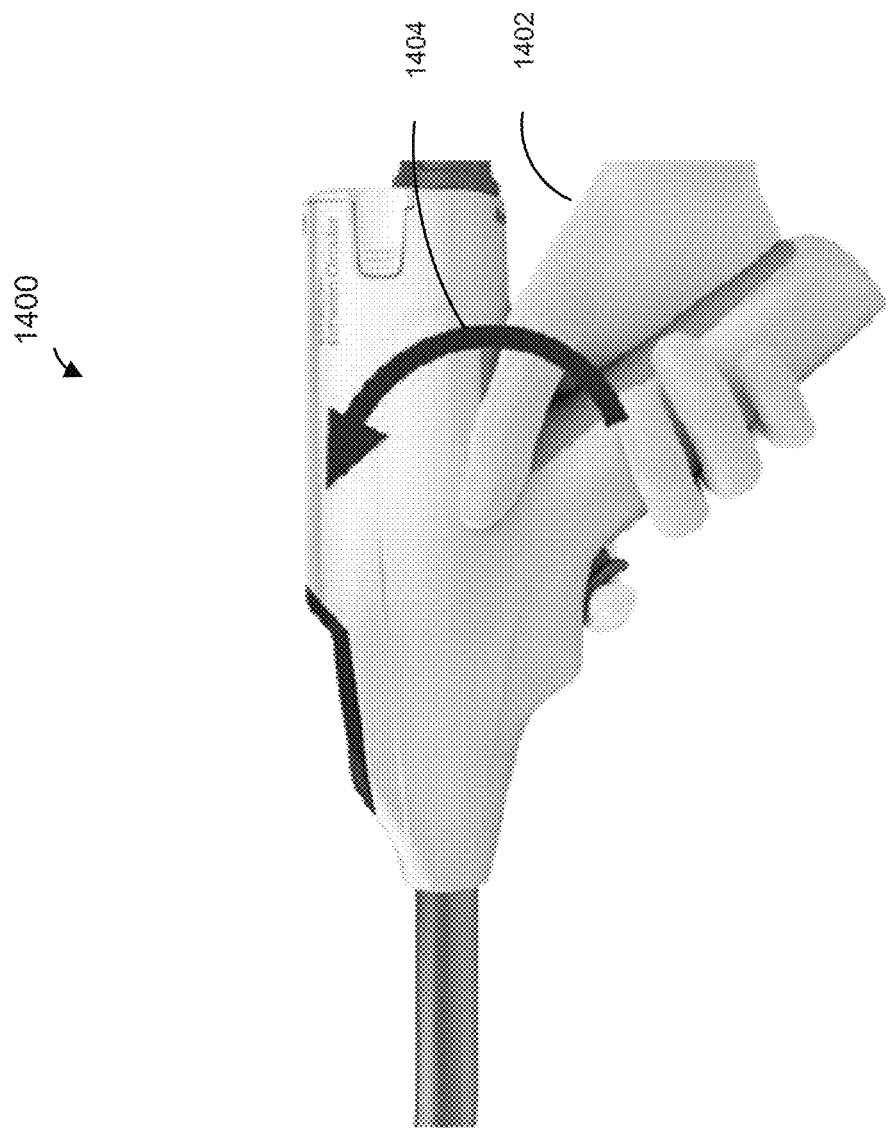
FIGS. 14A-B depict example graphics that may be used to display a corrective action to guide a user of a surgical instrument to mitigate a force experienced by a shaft of the surgical instrument; and—
Figure 14B:
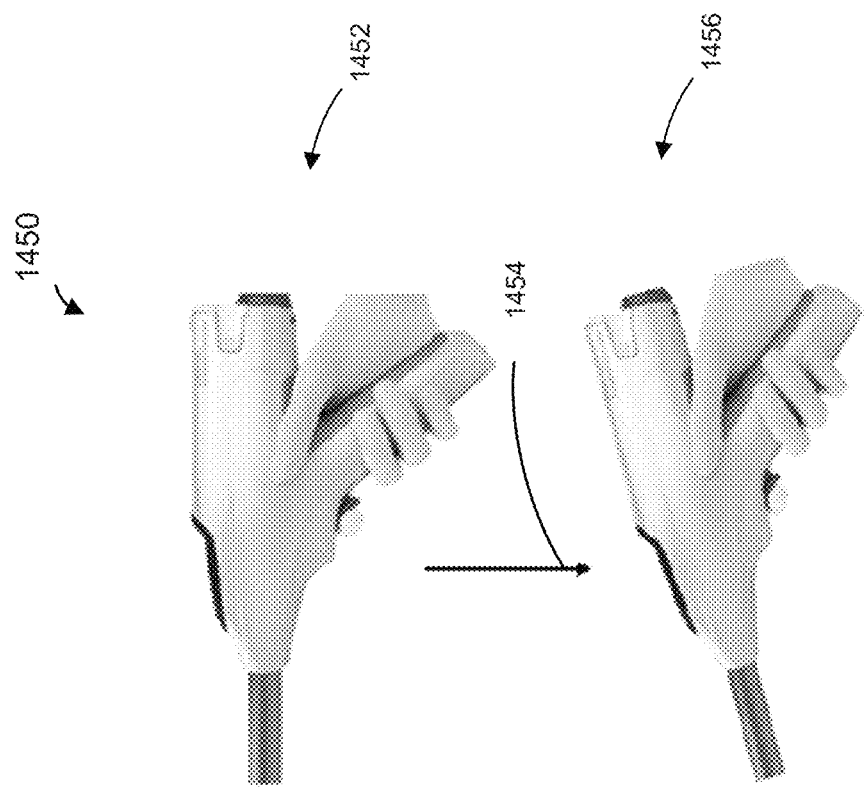

FIGS. 14A-B depict example of graphics 1400, 1450 that may be displayed to a user to inform the user of a corrective action that may be performed to mitigate an excessive force experienced by a shaft of a surgical instrument (e.g., the surgical instrument 1100). The graphics 1400, 1450 may be displayed on a display (e.g., a screen) of the handle portion 1110 of the surgical instrument 1100 or a computer that may be located in a room in which the surgical instrument 1100 is being used, for example. The graphics 1400, 1450 may provide a visual illustration of the handle portion 1110 and an indication of how to handle (e.g., rotate or otherwise move) the handle portion 1110 in order to reduce excessive forces experienced by the shaft 1108 of the surgical instrument 1100. Referring to FIG. 14A, the graphics 1400 include an illustration of a user's hand 1402 holding the handle portion 1110 and an arrow 1404 pointing in the clockwise direction. Accordingly, the user may be guided to rotate the handle portion 1110 in a direction indicated by the clockwise direction of the arrow 1404 in order to mitigate the force experienced by the shaft 1108. In this case, the user would be guided to tilt the distal end of the handle portion 1110 downward and/or the proximal end of the handle portion 1110 upward. Referring now to FIG. 14B, the graphics 1450 include an illustration 1452 of the user's hand holding the handle portion 1110 in a current position and an arrow 1454 guiding the user to an illustration 1456 illustrating the handle portion 1110 tilted down with respect to the current position. Accordingly, in this case, the user may be guided to tilt the handle portion 1110 down in order to mitigate the force experienced by the shaft 1108.

In some examples, various graphics may be provided in which the determined forces experienced by the shaft 1108 are continuously displayed. For example, a display of the determined forces experienced by the shaft 1108 may be provided as an overlay of the force on an illustration of the handle portion 1110 and/or the shaft 1108 to show the force being mitigated as the user is moving (e.g., rotating, tilting, etc.) the handle portion 1110. In other examples, other suitable graphics may be generated and displayed to alert the user of excessive force experienced by the shaft 1108, guide the user in order to mitigate the force, provide a real-time display of force as the user is moving the handle portion 1110, etc. Such graphics may help the user avoid "hang-ups" or causing any damage to a patient as the user maneuvers components of the surgical instrument 1100 inside the body of the patient.

Figure 15:
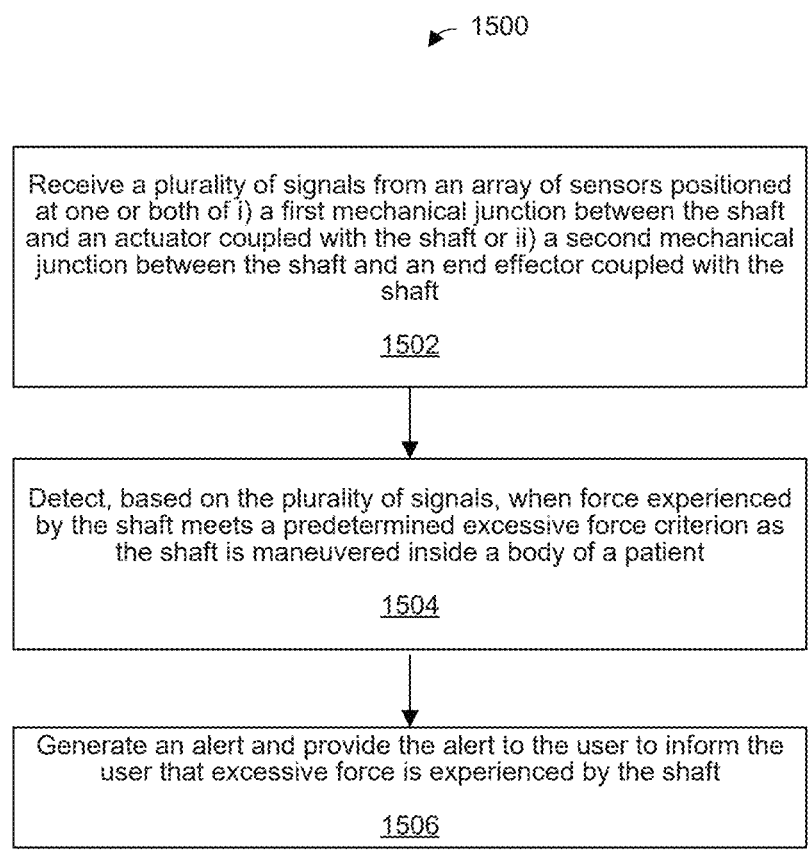
FIG. 15 is a flowchart of an example method for monitoring force experienced by a shaft of a surgical instrument as the shaft is maneuvered inside a body of a patient.

FIG. 15 is a flowchart of an example method 1500 for monitoring force experienced by a shaft of a surgical instrument as the shaft is maneuvered inside a body of a patient, according to an embodiment. In an embodiment, the method 1500 is implemented by the controller 1130 to monitor a force experienced by the shaft 1108 of the surgical instrument 1100 of FIG. 11. It is noted, however, that the method 1500 may be implemented by a controller different from the controller 1130 and/or with a surgical instrument different from the surgical instrument 1100 of FIG. 11, in other embodiments.

At a block 1502, the controller 1130 may receive a plurality of signals from a plurality of sensors positioned at one or both of i) a first mechanical junction between the shaft and an actuator coupled with the shaft or ii) a second mechanical junction between the shaft and an end effector coupled with the shaft. The actuator may include a handle portion of the surgical instrument, for example. In another example, the actuator may include a robotic arm attached to the shaft of the surgical instrument. The plurality of sensors may be configured to sense movement of the shaft relative to the actuator and/or the end effector as the shaft is being maneuvered inside the body of the patent. The signals generated by the sensors may thus be indicative of a force experienced by the shaft as the shaft is being maneuvered inside the body of the patent. In an example, the plurality of sensors may include sensors distributed among a plurality of points around the circumference of the shaft at the first mechanical junction and/or the second mechanical junction. The signals generated by the sensors may thus be indicative of forces experienced along the shaft at the plurality of points around the circumference of the shaft as the shaft is being maneuvered inside the body of the patent.

At a block 1504, the controller 1130 may detect, based on the plurality of signals, when force experienced by the shaft meets a predetermined excessive force criterion as the shaft is maneuvered inside the body of the patient. For example, the controller 1130 may determine, based on respective signals received from respective sensors among the plurality of sensors, respective forces experienced by the shaft at a plurality of points around the circumference of the shaft. The controller 1130 may compare the respective forces experienced by the shaft at the plurality of points around the circumference of the shaft with a predetermined threshold, and may determine that the force experienced by the shaft meets the predetermined excessive force criteria in response to determining that one or more forces, among the respective forces, exceeds the predetermined threshold. In an embodiment, the controller 1130 may also be configured to further process the signals received from the plurality of sensors, for example to determine a magnitude and/or direction of the force experienced by the shaft.

At a block 1506, the controller 1130 may generate an alert and may provide the alert to the user to inform the user that the shaft is experiencing excessive force. The controller 1130 may generate the alert at block 1506 in response to detecting at block 1504 that the force experienced by the shaft meets the predetermined excessive force criterion. The alert may comprise a haptic feedback signal that may be provided via the handle portion of the surgical instrument, for example. Additionally or alternatively, a visual and/or auditory alert may be provided. The alert may alert the user that the user should ease up on pushing the surgical instrument, and/or reposition the surgical instrument, in order to mitigate the force and avoid harming the patient. In some embodiments, additional information regarding the force may be provided to the user. For example, a display of the magnitude and/or direction of the force may be provided to the user, for example, on a screen located on the handle portion of the surgical instrument or in an operating room in which the surgical instrument is being used. Such additional information may inform the user of the degree to which the user should ease up and/or a direction in which the user should move the surgical instrument to mitigate the force.

In some embodiments, the controller may be further configured to determine a corrective action that may be performed by the user in order to mitigate the excessive force. In such embodiments, an indication of the corrective action may be provided to the user, for example via the screen or other display on the handle portion of the surgical instrument or in the operating room in which the surgical instrument is being used.

The embodiments disclosed herein provide a shaft detection system configured to detect movement of the shaft of a surgical instrument relative to another component of the surgical instrument. The movement of the shaft may be indicative of a force, pressure, strain, etc. experienced by the shaft as the surgical instrument is maneuvered inside a body of a patient. The shaft detection system may thus provide indication of when excessive force is being experienced by the shaft and/or provide indications of corrective actions that may be taken to mitigate the force as the shaft is being maneuvered inside the body of the patient. These and other techniques described herein may reduce chances of causing harm to the patient due to forceful pushing of components of the surgical instrument against anatomy inside the body of the patient, such as during insertion the surgical instrument into or removal of the surgical instrument from the body of the patient.

III. Examples of Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

1. A surgical instrument, comprising:
   a shaft configured to couple with an actuator at a first mechanical junction between the shaft and the actuator;
   an end effector coupled with the shaft at a second mechanical junction between the shaft and the end effector, wherein i) the end effector is configured to clamp, staple, and cut tissue and ii) the actuator is configured to operate the end effector via the shaft, and wherein the shaft is one or both i) movable relative to the actuator at the first mechanical junction between the shaft and the actuator or ii) movable relative to the end effector at the second mechanical junction between the shaft and the end effector; and
   a shaft deflection detection system including one or more sensors positioned at one or both of the first mechanical junction or the second mechanical junction, wherein the one or more sensors are configured to generate signals indicative of movement of the shaft relative to one or both of the actuator or the end effector, wherein the movement of the shaft is caused by an external force experienced by the shaft as the shaft of the surgical instrument is maneuvered inside a body of a patient.

2. The surgical instrument of claim 1, wherein:
   the end effector comprises a circular stapler; and
   the one or more sensors are configured to detect movement of the shaft relative to the one or both of the actuator or the end effector as the shaft of the surgical instrument is maneuvered inside an anatomical lumen in the body of the patient.

3. The surgical instrument of claim 1, wherein the one or more sensors comprise a plurality of sensors distributed among a plurality of points around a circumference of the shaft at one or both of i) the first mechanical junction between the shaft and the actuator or ii) the second mechanical junction between the shaft and the end effector.

4. The surgical instrument of claim 3, further comprising a controller communicatively coupled to the shaft deflection detection system, the controller configured to:
   receive respective signals generated by respective sensors among the plurality of sensors;
   determine, based on the respective signals generated by respective sensors among the plurality of sensors, respective forces experienced by the shaft at respective points among the plurality of points around the circumference of the shaft;
   compare the respective forces experienced by the shaft at the respective points to a predetermined threshold; and
   determine that excessive force is experienced at one or more points around the circumference of the shaft in response to determining that one or more forces, among the respective forces, exceeds the predetermined threshold.

5. The surgical instrument of claim 4, wherein the controller is further configured to, in response to determining that excessive force is experienced by the shaft at one or more points around the circumference of the shaft, generate an alert and provide the alert to a user of the surgical instrument to inform the user that excessive force is experienced by the shaft.

6. The surgical instrument of claim 5, wherein the alert is a haptic buzz provided to the user via a handle portion of the surgical instrument.

7. The surgical instrument of claim 5, wherein the controller is further configured to determine, based on the respective signals generated by respective sensors among the plurality of sensors, a magnitude and a direction of the external force experienced by the shaft.

8. The surgical instrument of claim 7, wherein the controller is further configured to:
   determine, based on one or both of the magnitude or the direction of the external force, a corrective action to mitigate the excessive force experienced by the shaft; and
   provide an indication of the corrective action to the user to enable the user to mitigate the excessive force experienced by the shaft.

9. The surgical instrument of claim 7, wherein the controller is further configured to:
   generate real-time graphics illustrating one or both of the direction or the magnitude of the external force experienced by the shaft as the user is maneuvering the shaft of the surgical instrument inside the body of the patient; and
   cause the real-time graphics to be displayed to the user.

10. The surgical instrument of claim 4, wherein:
    the plurality of sensors comprises a plurality of Hall effect sensors positioned at the first mechanical junction on an outer surface of the shaft at the plurality of points around the circumference of the shaft; and
    the shaft deflection detection system further includes
    a plurality of magnets positioned at the first mechanical junction at a plurality of points on an inner surface of the actuator coupled with the shaft such that respective magnets among the plurality of magnets are positioned across from respective sensors among the plurality of Hall effect sensors, and
    a plurality of springs positioned in spaces between respective sensors among the plurality of Hall effect sensors, the springs being coupled between the outer surface of the shaft and the inner surface of the actuator coupled with the shaft such that the springs compress or decompress with movement of the shaft relative to the actuator coupled with the shaft, wherein the springs are characterized by a predetermined spring force function.

11. The surgical instrument of claim 10, wherein the controller is configured to determine respective forces experienced along the shaft at the plurality of points around the circumference of the shaft based on i) the signals indicative of the movement of the shaft received from respective sensors among the plurality of Hall effect sensors and ii) the predetermined spring force function.

12. The surgical instrument of claim 1, wherein the actuator comprises a manually operated handle portion coupled with the shaft.

13. The surgical instrument of claim 1, wherein the actuator comprises a robotic arm attached to the shaft.

14. A surgical instrument, comprising:
a shaft;
a handle portion coupled with the shaft, wherein the shaft is movable relative to the handle portion at a mechanical junction between the handle portion and the shaft; and
a shaft deflection detection system including a plurality of sensors positioned at the mechanical junction between the handle portion and the shaft,
wherein sensors among the plurality of sensors are distributed at a plurality of points around a circumference of the shaft, and wherein the sensors among the plurality of sensors are configured to generate signals indicative of external forces experienced along the shaft at the plurality of points around the circumference of the shaft as the shaft of the surgical instrument is maneuvered inside a body of a patient.

15. The surgical instrument of claim 14, wherein:
the surgical instrument further comprises a circular stapler end effector coupled with the shaft; and
the plurality of sensors is configured to detect movement of the shaft relative to the handle portion as the shaft of the surgical instrument is maneuvered inside an anatomical lumen in the body of the patient.

16. The surgical instrument of claim 14, further comprising a controller communicatively coupled with the shaft deflection detection system, the controller configured to:
receive the signals generated by the sensors among the plurality of sensors;
detect, based on the signals generated by the sensors among the plurality of sensors, when excessive force is experienced by the shaft at one or more points among the plurality of points around the circumference of the shaft; and
in response to detecting that excessive force is experienced by the shaft at one or more points around the circumference of the shaft, generate an alert and provide the alert to a user of the surgical instrument to inform the user that excessive force is experienced by the shaft.

17. The surgical instrument of claim 16, wherein the controller is further configured to:
determine, based on the signals generated by the sensors among the plurality of sensors, a magnitude and a direction of the excessive force experienced by the shaft;
determine, based on one or both of the magnitude and the direction of the external force, a corrective action to mitigate the excessive force experienced by the shaft; and provide an indication of the corrective action to the user to enable the user to mitigate the excessive force experienced by the shaft.

18. The surgical instrument of claim 16, wherein:
the plurality of sensors comprises a plurality of Hall effect sensors positioned at the mechanical junction on an outer surface of the shaft at a plurality of points around the circumference of the shaft;
the shaft deflection detection system further includes
a plurality of magnets positioned at the mechanical junction at a plurality of points on an inner surface of the handle portion coupled with the shaft such that respective magnets among the plurality of magnets are positioned across from respective sensors among the plurality of Hall effect sensors, and
a plurality of springs positioned in spaces between respective sensors among the plurality of Hall effect sensors, the springs being coupled between the outer surface of the shaft and the inner surface of the handle portion coupled with the shaft such that the springs compress or decompress with movement of the shaft relative to the handle portion coupled with the shaft, wherein the springs are characterized by a predetermined spring force function; and
the controller is configured to determine respective forces experienced along the shaft at the plurality of points around the circumference of the shaft based on i) the signals indicative of the movement of the shaft received from respective sensors among the plurality of Hall effect sensors and ii) the predetermined spring force function.

19. A method for monitoring force experienced by a shaft of a surgical instrument as the shaft is maneuvered inside a body of a patient, the method comprising:
receiving, at a controller of the surgical instrument, a plurality of signals from a plurality of sensors positioned at one or both of i) a first mechanical junction between the shaft and an actuator coupled with the shaft or ii) a second mechanical junction between the shaft and an end effector coupled with the shaft, the plurality of sensors distributed among a plurality of points around a circumference of the shaft at the one or both of the first mechanical junction and the second mechanical junction;
detecting, by the controller based on the plurality of signals, that force experienced by the shaft meets a predetermined excessive force criterion as the shaft is maneuvered inside the body of the patient; and
in response to detecting that the force experienced by the shaft meets the predetermined excessive force criterion, generating, by the controller, an alert and providing the alert to a user to inform the user that excessive force is experienced by the shaft.

20. The method of claim 19, wherein detecting when the force experienced by the shaft meets the predetermined excessive force criterion includes:
determining, based on respective signals generated by respective sensors among the plurality of sensors, respective forces experienced by the shaft at a plurality of points around the circumference of the shaft;
comparing the respective forces experienced by the shaft at the plurality of points around the circumference of the shaft with a predetermined threshold; and
detecting that the force experienced by the shaft meets the predetermined excessive force criterion in response to determining that one or more forces, among the respective forces, exceeds the predetermined threshold.

IV. Miscellaneous

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

Furthermore, any one or more of the teachings herein may be combined with any one or more of the teachings disclosed in U.S. Pat. App. No. 63/467,622, entitled "Surgical Stapler Cartridge Having Intermediate Raised Tissue Engagement Protrusions," filed on May 19, 2023; U.S. Pat. App. No. 63/467,623, entitled "Surgical Stapler Cartridge Having Tissue Engagement Protrusions with Enlarged Engagement Surface," filed on May 19, 2023; U.S. Pat. App. No. 63/467,648, entitled "Surgical Stapler Cartridge Having Raised Surface to Promote Buttress Adhesion," filed on May 19, 2023; U.S. Pat. App. No. 63/467,469, entitled "Surgical Stapler Cartridge Having Cartridge Retention Features," filed on May 19, 2023; U.S. Pat. App. No. 63/459,739, entitled "Surgical Stapler Anvil Having Staple Forming Pockets with Laterally Varying Orientations," filed on May 19, 2023; U.S. Pat. App. No. 63/467,656, entitled "Surgical Stapler With Discretely Positionable Distal Tip," filed on May 19, 2023; and/or U.S. Pat. App. No. 63/467,615, entitled "Incompatible Staple Cartridge Use Prevention Features for Surgical Stapler," filed on May 19, 2023.

Additionally, any one or more of the teachings herein may be combined with any one or more of the teachings disclosed in U.S. Pat. App. No. 63/459,739, entitled "Surgical Stapler Anvil Having Staple Forming Pockets with Laterally Varying Orientations," filed on Apr. 17, 2023. The disclosure of each of these U.S. patent applications is incorporated by reference herein in its entirety.

Additionally, any one or more of the teachings herein may be combined with any one or more of the teachings disclosed in U.S. Pat. No. 11,304,697, entitled "Surgical Stapler with Deflectable Distal Tip," issued Apr. 19, 2022, the disclosure of which is incorporated by reference herein, in its entirety; U.S. Pat. No. 11,317,912, entitled "Surgical Stapler with Rotatable Distal Tip," issued May 3, 2022, the disclosure of which is incorporated by reference herein, in its entirety; and/or U.S. Pat. No. 11,439,391, entitled "Surgical Stapler with Toggling Distal Tip," issued Sep. 13, 2022, the disclosure of which is incorporated by reference herein, in its entirety.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as those made available by Auris Health, Inc. of Redwood City, CA or by Intuitive Surgical, Inc., of Sunnyvale, California.

Versions of the devices described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

What is claimed is:

1. A surgical instrument, comprising:
   a shaft configured to couple with an actuator at a first mechanical junction between the shaft and the actuator;
   an end effector coupled with the shaft at a second mechanical junction between the shaft and the end effector, wherein i) the end effector is configured to clamp, staple, and cut tissue and ii) the actuator is configured to operate the end effector via the shaft, and wherein the shaft is one or both i) movable relative to the actuator at the first mechanical junction between the shaft and the actuator or ii) movable relative to the end effector at the second mechanical junction between the shaft and the end effector; and
   a shaft deflection detection system including one or more sensors positioned at one or both of the first mechanical junction or the second mechanical junction, wherein the one or more sensors are configured to generate signals indicative of movement of the shaft relative to one or both of the actuator or the end effector, wherein the movement of the shaft is caused by an external force experienced by the shaft as the shaft of the surgical instrument is maneuvered inside a body of a patient.

2. The surgical instrument of claim 1, wherein:
the end effector comprises a circular stapler; and
the one or more sensors are configured to detect movement of the shaft relative to the one or both of the actuator or the end effector as the shaft of the surgical instrument is maneuvered inside an anatomical lumen in the body of the patient.

3. The surgical instrument of claim 1, wherein the one or more sensors comprise a plurality of sensors distributed among a plurality of points around a circumference of the shaft at one or both of i) the first mechanical junction between the shaft and the actuator or ii) the second mechanical junction between the shaft and the end effector.

4. The surgical instrument of claim 3, further comprising a controller communicatively coupled to the shaft deflection detection system, the controller configured to:
receive respective signals generated by respective sensors among the plurality of sensors;
determine, based on the respective signals generated by respective sensors among the plurality of sensors, respective forces experienced by the shaft at respective points among the plurality of points around the circumference of the shaft;
compare the respective forces experienced by the shaft at the respective points to a predetermined threshold; and
determine that excessive force is experienced at one or more points around the circumference of the shaft in response to determining that one or more forces, among the respective forces, exceeds the predetermined threshold.

5. The surgical instrument of claim 4, wherein the controller is further configured to, in response to determining that excessive force is experienced by the shaft at one or more points around the circumference of the shaft, generate an alert and provide the alert to a user of the surgical instrument to inform the user that excessive force is experienced by the shaft.

6. The surgical instrument of claim 5, wherein the alert is a haptic buzz provided to the user via a handle portion of the surgical instrument.

7. The surgical instrument of claim 5, wherein the controller is further configured to determine, based on the respective signals generated by respective sensors among the plurality of sensors, a magnitude and a direction of the external force experienced by the shaft.

8. The surgical instrument of claim 7, wherein the controller is further configured to:
determine, based on one or both of the magnitude or the direction of the external force, a corrective action to mitigate the excessive force experienced by the shaft; and
provide an indication of the corrective action to the user to enable the user to mitigate the excessive force experienced by the shaft.

9. The surgical instrument of claim 7, wherein the controller is further configured to:
generate real-time graphics illustrating one or both of the direction or the magnitude of the external force experienced by the shaft as the user is maneuvering the shaft of the surgical instrument inside the body of the patient; and
cause the real-time graphics to be displayed to the user.

10. The surgical instrument of claim 4, wherein:
the plurality of sensors comprises a plurality of Hall effect sensors positioned at the first mechanical junction on an outer surface of the shaft at the plurality of points around the circumference of the shaft; and
the shaft deflection detection system further includes
a plurality of magnets positioned at the first mechanical junction at a plurality of points on an inner surface of the actuator coupled with the shaft such that respective magnets among the plurality of magnets are positioned across from respective sensors among the plurality of Hall effect sensors, and
a plurality of springs positioned in spaces between respective sensors among the plurality of Hall effect sensors, the springs being coupled between the outer surface of the shaft and the inner surface of the actuator coupled with the shaft such that the springs compress or decompress with movement of the shaft relative to the actuator coupled with the shaft, wherein the springs are characterized by a predetermined spring force function.

11. The surgical instrument of claim 10, wherein the controller is configured to determine respective forces experienced along the shaft at the plurality of points around the circumference of the shaft based on i) the signals indicative of the movement of the shaft received from respective sensors among the plurality of Hall effect sensors and ii) the predetermined spring force function.

12. The surgical instrument of claim 1, wherein the actuator comprises a manually operated handle portion coupled with the shaft.

13. The surgical instrument of claim 1, wherein the actuator comprises a robotic arm attached to the shaft.

14. A surgical instrument, comprising:
a shaft;
a handle portion coupled with the shaft, wherein the shaft is movable relative to the handle portion at a mechanical junction between the handle portion and the shaft; and
a shaft deflection detection system including a plurality of sensors positioned at the mechanical junction between the handle portion and the shaft,
wherein sensors among the plurality of sensors are distributed at a plurality of points around a circumference of the shaft, and wherein the sensors among the plurality of sensors are configured to generate signals indicative of external forces experienced along the shaft at the plurality of points around the circumference of the shaft as the shaft of the surgical instrument is maneuvered inside a body of a patient.

15. The surgical instrument of claim 14, wherein:
the surgical instrument further comprises a circular stapler end effector coupled with the shaft; and
the plurality of sensors is configured to detect movement of the shaft relative to the handle portion as the shaft of the surgical instrument is maneuvered inside an anatomical lumen in the body of the patient.

16. The surgical instrument of claim 14, further comprising a controller communicatively coupled with the shaft deflection detection system, the controller configured to:
receive the signals generated by the sensors among the plurality of sensors;
detect, based on the signals generated by the sensors among the plurality of sensors, when excessive force is experienced by the shaft at one or more points among the plurality of points around the circumference of the shaft; and
in response to detecting that excessive force is experienced by the shaft at one or more points around the circumference of the shaft, generate an alert and provide the alert to a user of the surgical instrument to inform the user that excessive force is experienced by the shaft.

17. The surgical instrument of claim 16, wherein the controller is further configured to:
   determine, based on the signals generated by the sensors among the plurality of sensors, a magnitude and a direction of the excessive force experienced by the shaft;
   determine, based on one or both of the magnitude and the direction of the external force, a corrective action to mitigate the excessive force experienced by the shaft; and
   provide an indication of the corrective action to the user to enable the user to mitigate the excessive force experienced by the shaft.

18. The surgical instrument of claim 16, wherein:
   the plurality of sensors comprises a plurality of Hall effect sensors positioned at the mechanical junction on an outer surface of the shaft at a plurality of points around the circumference of the shaft;
   the shaft deflection detection system further includes
      a plurality of magnets positioned at the mechanical junction at a plurality of points on an inner surface of the handle portion coupled with the shaft such that respective magnets among the plurality of magnets are positioned across from respective sensors among the plurality of Hall effect sensors, and
      a plurality of springs positioned in spaces between respective sensors among the plurality of Hall effect sensors, the springs being coupled between the outer surface of the shaft and the inner surface of the handle portion coupled with the shaft such that the springs compress or decompress with movement of the shaft relative to the handle portion coupled with the shaft, wherein the springs are characterized by a predetermined spring force function; and
   the controller is configured to determine respective forces experienced along the shaft at the plurality of points around the circumference of the shaft based on i) the signals indicative of the movement of the shaft received from respective sensors among the plurality of Hall effect sensors and ii) the predetermined spring force function.

19. A method for monitoring force experienced by a shaft of a surgical instrument as the shaft is maneuvered inside a body of a patient, the method comprising:
   receiving, at a controller of the surgical instrument, a plurality of signals from a plurality of sensors positioned at one or both of i) a first mechanical junction between the shaft and an actuator coupled with the shaft or ii) a second mechanical junction between the shaft and an end effector coupled with the shaft, the plurality of sensors distributed among a plurality of points around a circumference of the shaft at the one or both of the first mechanical junction and the second mechanical junction;
   detecting, by the controller based on the plurality of signals, that force experienced by the shaft meets a predetermined excessive force criterion as the shaft is maneuvered inside the body of the patient; and
   in response to detecting that the force experienced by the shaft meets the predetermined excessive force criterion, generating, by the controller, an alert and providing the alert to a user to inform the user that excessive force is experienced by the shaft.

20. The method of claim 19, wherein detecting when the force experienced by the shaft meets the predetermined excessive force criterion includes:
   determining, based on respective signals generated by respective sensors among the plurality of sensors, respective forces experienced by the shaft at a plurality of points around the circumference of the shaft;
   comparing the respective forces experienced by the shaft at the plurality of points around the circumference of the shaft with a predetermined threshold; and
   detecting that the force experienced by the shaft meets the predetermined excessive force criterion in response to determining that one or more forces, among the respective forces, exceeds the predetermined threshold.

\* \* \* \* \*